United States Patent
Swendseid et al.

(10) Patent No.: US 9,161,574 B2
(45) Date of Patent: *Oct. 20, 2015

(54) POST-SURGICAL GARMENT

(75) Inventors: Jennifer V. Swendseid, St. Louis Park, MN (US); Diane McMonigal-Paterson, Mendota Heights, MN (US)

(73) Assignee: Heart & Core, LLC, St. Louis Park, MN (US)

(*) Notice: Subject to any disclaimer, the term of this patent is extended or adjusted under 35 U.S.C. 154(b) by 346 days.

This patent is subject to a terminal disclaimer.

(21) Appl. No.: 13/601,764

(22) Filed: Aug. 31, 2012

(65) Prior Publication Data

US 2013/0171911 A1 Jul. 4, 2013

Related U.S. Application Data

(63) Continuation-in-part of application No. 13/461,982, filed on May 2, 2012, now Pat. No. 8,460,054, which is a continuation of application No. 12/688,582, filed on Jan. 15, 2010, now Pat. No. 8,172,639.

(51) Int. Cl.
*A41C 3/08* (2006.01)
*A41C 3/00* (2006.01)
(Continued)

(52) U.S. Cl.
CPC ............. *A41C 3/0064* (2013.01); *A41C 3/0028* (2013.01); *A41C 3/0057* (2013.01); *A61F 13/00068* (2013.01); *A61F 13/145* (2013.01);
(Continued)

(58) Field of Classification Search
CPC ....................................................... A41C 3/00

USPC ............ 450/1, 3–8, 19–21, 36, 38, 39, 54, 55, 450/58, 60–63
See application file for complete search history.

(56) References Cited

U.S. PATENT DOCUMENTS 3,362,409 A    1/1968  Bruno
3,826,266 A *  7/1974  Alpert .............................. 450/11
(Continued)

FOREIGN PATENT DOCUMENTS

AU    2007203134    1/2008
JP    2003221705    8/2003
WO    WO2010102348    9/2010

OTHER PUBLICATIONS

International Search Report for PCT Application No. PCT/AU2010/000290 mailed Apr. 23, 2010, 4 pgs.
(Continued)

*Primary Examiner* — Gloria Hale
(74) *Attorney, Agent, or Firm* — Dicke, Billig & Czaja, PLLC

(57) ABSTRACT

A post medical procedure garment includes front and rear panels with height adjusting straps that extend over the wearer's shoulders. The front panel includes an outer compression fabric and an inner cup assembly, which is essentially non-compressive. The cup assembly includes individual cups for each breast. An elastic band extends around the bottom portion of the garment. Tensioning structures, such as side flaps extending from the back to the front, can be provided to adjust the circumferential size of the garment. The garment can include releasable closures on the side of the garment to aid in putting on and taking off the garment. A connector can removably attach a fluid storage device to the side flaps or the elastic band. The fluid storage device can hold post-medical procedure drainage fluid.

24 Claims, 22 Drawing Sheets

(51) Int. Cl.
*A61F 13/14* (2006.01)
*A61F 13/00* (2006.01)

(52) U.S. Cl.
CPC ......... *A41C 3/08* (2013.01); *A61F 2013/00536* (2013.01)

(56) References Cited

U.S. PATENT DOCUMENTS

| | | | |
|---|---|---|---|
| 4,289,137 | A | 9/1981 | Dell et al. |
| 4,432,364 | A | 2/1984 | Martini |
| 4,583,544 | A | 4/1986 | Flanagan et al. |
| 4,781,651 | A | 11/1988 | Ekins |
| 4,816,005 | A | 3/1989 | Braaten |
| 4,909,771 | A | 3/1990 | Bergman |
| 5,211,598 | A | 5/1993 | Hall |
| 5,823,851 | A | 10/1998 | Dicker |
| 5,967,877 | A | 10/1999 | Howard |
| 6,068,538 | A | 5/2000 | Alleyne |
| 6,165,045 | A | 12/2000 | Miller et al. |
| D438,691 | S | 3/2001 | Zagame |
| 6,390,885 | B1 * | 5/2002 | Brooks ............................. 450/1 |
| 6,514,120 | B1 | 2/2003 | Hass |
| 6,572,437 | B1 | 6/2003 | Waitz |
| 6,610,032 | B1 | 8/2003 | Prody |
| 6,860,789 | B2 * | 3/2005 | Bell et al. ........................ 450/20 |
| 7,089,597 | B2 | 8/2006 | Horii et al. |
| 7,144,294 | B2 * | 12/2006 | Bell et al. ........................ 450/20 |
| 7,207,861 | B2 | 4/2007 | Martini |
| 7,309,276 | B2 | 12/2007 | Legaspi et al. |
| 7,381,113 | B2 | 6/2008 | Hori |
| 7,435,155 | B2 | 10/2008 | Reinisch et al. |
| D594,631 | S | 6/2009 | Reinisch |
| 7,549,971 | B2 * | 6/2009 | Bell et al. ........................ 602/75 |
| 7,909,675 | B1 | 3/2011 | Rainey |
| D635,329 | S | 4/2011 | Wahl et al. |
| 7,922,682 | B2 * | 4/2011 | Bell et al. ........................ 602/75 |
| 2001/0019933 | A1 | 9/2001 | Wagner |
| 2004/0002288 | A1 * | 1/2004 | Bell et al. ........................ 450/75 |
| 2005/0009445 | A1 * | 1/2005 | Bell et al. ......................... 450/1 |
| 2006/0019576 | A1 * | 1/2006 | Bell et al. ........................ 450/60 |
| 2006/0048547 | A1 | 3/2006 | Duckham et al. |
| 2006/0252346 | A1 | 11/2006 | Reinisch et al. |
| 2009/0259159 | A1 * | 10/2009 | Bell et al. ........................ 602/75 |
| 2010/0177757 | A1 * | 7/2010 | Kim et al. ...................... 370/338 |
| 2012/0220192 | A1 * | 8/2012 | Swendseid ...................... 450/85 |
| 2013/0171911 | A1 * | 7/2013 | Swendseid et al. ............. 450/85 |

OTHER PUBLICATIONS

Heart&Core, LLC; Signature Line Sports Bras; www.heartandcare.com/Sports_Bras.html; Dec. 2009; 1 pg.
Casselman; The Physics of Bras: Overcoming Newton's Second Law With Better Bra Technology; Discover Magazine; http://discovermagazine.com/2005/nov/physics-of-bras/article_print; Nov. 22, 2005; 3 pgs.
Berlei; Getting Fitted Is Just As Important As Getting Fit!; http://www.berlei.com.au/news/newsitem.aspx?id=24; Feb. 12, 2010; 1 pg.
McGhee et al.; Breast Elevation and Compression Decreases Exercise-Induced Breast Discomfort; Medicine & Science, Sports & Exercise: The Official Journal of the American College of Sports Medicine; Nov. 9, 2009; 22 pgs.
Mills; The Intelligent Bra That Takes the Jiggling Out of Jogging; Mail Online; http://www.dailymail.co.uk/sciencetech/article-500874; Dec. 9, 2007; 6 pgs.
Autospeed; Designing the Perfect Bra; http://autospeed.com/A_1260/cms/article.html; Jan. 22, 2002; 5 pgs.
Tomima; (Un)covering What's Under Everything: More Study on Breast Movement and Breast Pain; http://www.tomima.com/2009/12/09/more-study-on-breast-movement-and-breast-pain/; Dec. 2009; 5 pgs.
Good Read; Quest to Make the Perfect Fit Bra; http://spoonfeedin.blogspot.com/2008/06/quest-to-make-perfect-fit-bra.html; Jun. 24, 2008; 7 pgs.
Lawson et al.; Selected Sports Bras: Comparisons of Comfort and Support; Clothing and Textiles Research Journal; http://ctr.sagepub.com/cgi/content/abstract/8/4/55; 1990, 1 pg.
ABC Science Online; Smart Bra to Give Support When It's Needed; http://www.abc.net.au/science/news/stories/s131388.htm; May 26, 2000; 2 pgs.
Starr et al.; Biomechanical Analysis of a Prototype Sports Bra; Journal of Textile and Apparel, Technology and Management, vol. 4, Issue 3; Spring 2005; 14 pgs.

* cited by examiner

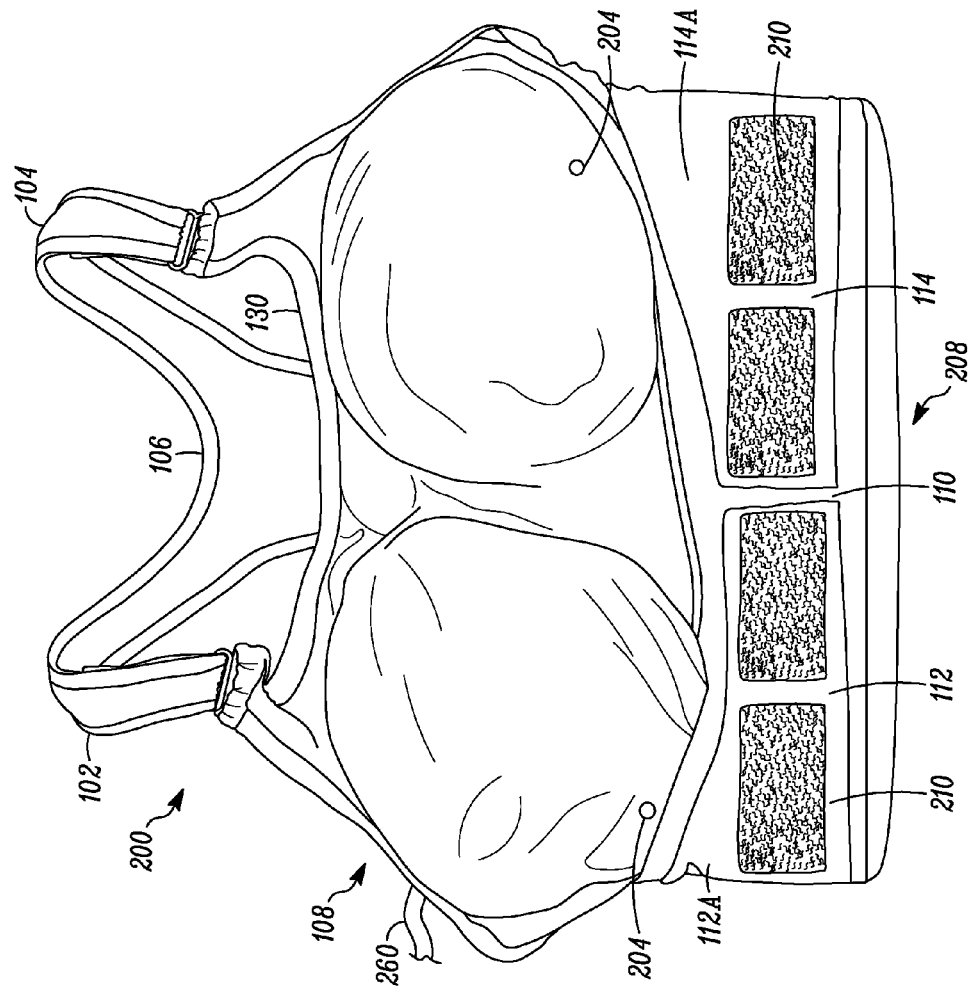
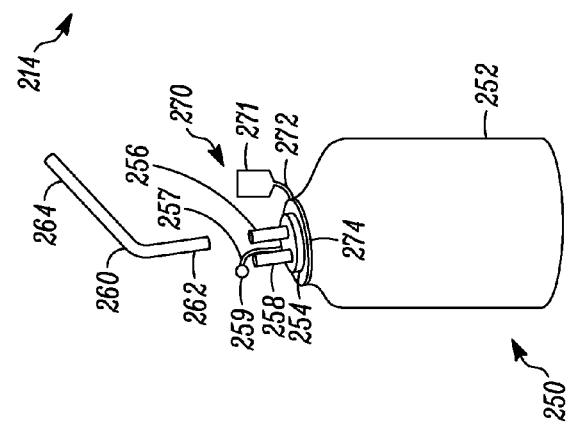
FIG. 13A

POST-SURGICAL GARMENT

This application is a continuation-in-part of U.S. patent application Ser. No. 13/461,982, now U.S. Pat. No. 8,460,054, filed 2 May 2012, which is a Continuation of U.S. patent application Ser. No. 12/688,582, now U.S. Pat. No. 8,172,639, both applications are hereby incorporated by reference in their entirety for any purpose.

FIELD

This application relates generally to a garment worn by females, and, more specifically, to an undergarment and brassiere for wear after a medical procedure or a surgical procedure, for example, a mastectomy, cardiac or other procedure involving breast tissue or upper body.

BACKGROUND

Women wear sports brassieres (bras) to support their breasts and reduce the bounce that can be experienced during exercise for comfort. Research has shown that ill fitting bras, commonly worn by many women, can result in damage to the fragile ligaments, which can be irreparably stretched, broken collar bones from sudden movement, and possibly nerve damage. These issues can be of even greater importance to larger chested women. If a woman experiences pain or discomfort during exercise, she may decide to stop exercising, which may be detrimental to her overall health. The present inventor has determined that this can be a more significant problem, which has not been adequately addressed by current sports bras.

A mastectomy is a surgical procedure for removal of a portion of or the entire breast, usually to remove cancerous tissue. The operation can be performed in a hospital or in an outpatient clinic, depending on the extent of the operation. The operation takes from two to three hours. Three to five weeks are needed for full recovery.

Drainage shunts are left in the surgical incision for a few days after the operation; these typically are removed in five to seven days if the area is healing normally. The drainage shunt removes fluids from the surgical site. These fluids can include blood, lymph fluid and other bodily fluids. Without a drainage shunt, fluid buildup can cause problems with swelling, infection and pain. The drainage tubes extend out of an incision on the breast. The other end of the drainage tubes are connected to a collection container. The placement, retention and support of the collection container present a problem for the post surgical patient. The present inventor has determined that this can be a significant problem, which has not been adequately addressed by current garments.

BRIEF DESCRIPTION OF DRAWINGS

Embodiments are illustrated by way of example and not limitation in the figures of the accompanying drawings, in which like references indicate similar elements and in which:

FIG. 13A is a front view of a medical (e.g., mastectomy or post-surgical) garment in accordance with an example embodiment;

DETAILED DESCRIPTION

Figure 1A:
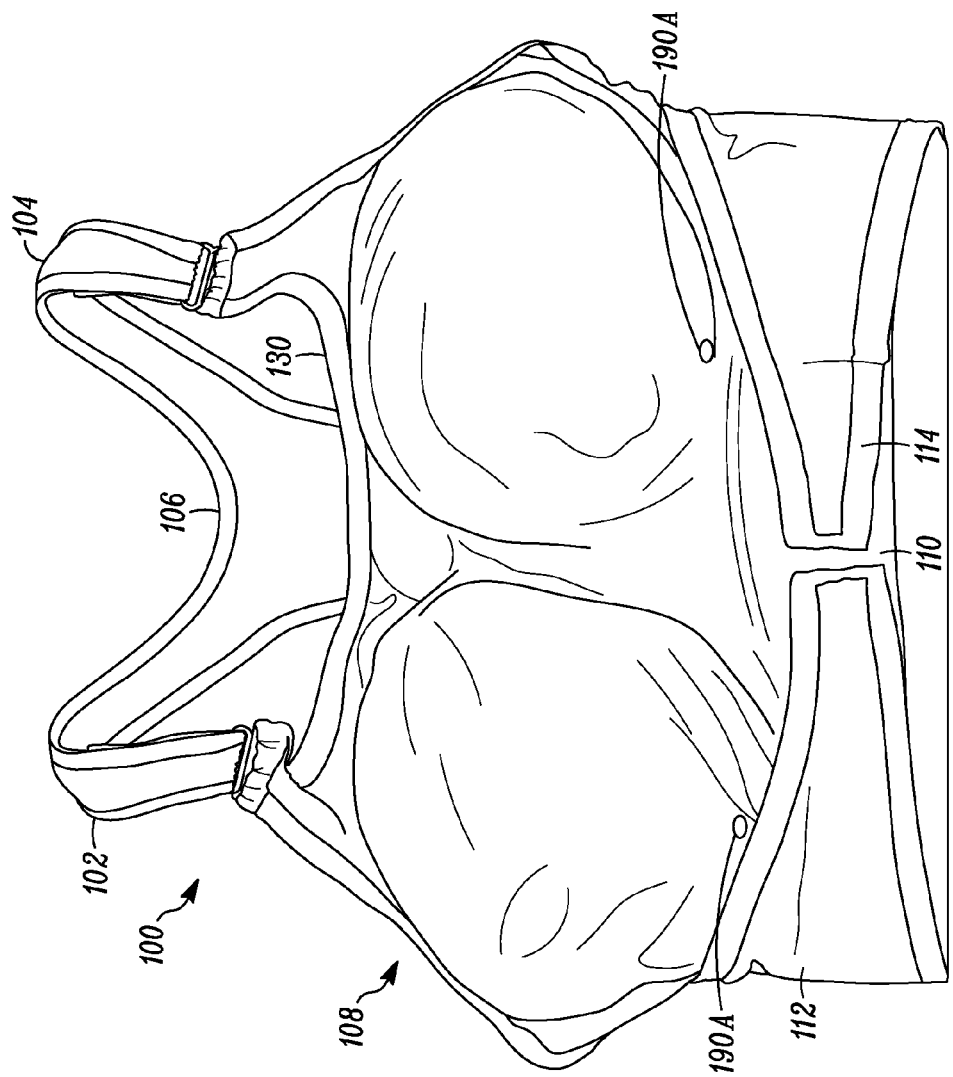
FIG. 1A is a front view of a garment in accordance with an example embodiment.

Example apparatuses, devices, methods and systems are described. In the following description, for purposes of explanation, numerous specific details are set forth in order to provide a thorough understanding of example embodiments. It will be evident, however, to one skilled in the art that the present invention can be practiced without these specific details.

In an example embodiment, an exercise garment includes a rear panel and a front panel connected to the rear panel. The front panel includes an elastic, outer cover fabric and a cup assembly to receive the breasts of the wearer. The cup assembly defines two cups that are joined by a bridge. The cup assembly encapsulates the wearer's breasts in an essentially non-stretchable fabric. The cover fabric can be elastic and can compress against the cup assembly to secure the wearer's breasts in place during exercise. An elastic band is positioned beneath the cup assembly to secure the garment on the torso of the wearer. Shoulder straps extend from the front panel to the rear panel. The garment further includes a circumferential tightening structure to tighten the circumference of the garment around the torso of the user. The circumferential tightening structure can engage the front of elastic band or the front panel to pull the front and rear panels together to tighten the garment or reduce the circumferential size of the garment.

Such a garment may be used as a post-medical procedure garment. In an example, the garment can be used with a wound drainage apparatus.

The shoulder straps can be adjustable in length to position the front panel vertically. To be adjustable the shoulder straps are cantilevered (e.g., fixed to the rear panel) from the rear panel and releasably connect to the front panel. The free ends of both the shoulder straps can lie over a portion of the respective first strap and second strap and secure thereto. Such shoulder straps may add additional benefits to a post-medical procedure wearer of the garment.

In an example, the circumferential tightening structure includes at least one side flap that in a first, free position is connected to only one of the front panel and the rear panel and in a second, tensioning position has another end that connects to the other of the front panel and rear panel. Flaps can be positioned on both sides of the garment. The rear sides of the flaps can be fixedly connected to the rear panel and extend essentially the height of the rear panel. The flaps can include a narrower end that is adapted to wrap around to the front panel and engage at least one of the front panel and the band to tension the garment around the torso of the wearer.

The band is positioned on the bottom of the garment and can have one part of a hook and loop connector. The flaps can include the other part of a hook and loop connector such that hook and loop connector releasably joins the flaps to the front of the band. The connector can release tension between the front panel and rear panel to assist in removing the garment from the wearer.

The garment can be a shirt that has an extension connected to the front and rear panel. The shirt extension can extend downwardly to cover a lower part of a torso of a wearer.

In an example, the cups can each include an under support to assist in lifting the wearer's breasts. In an example, the under support includes a foam material. Other semi-rigid materials, e.g., a plastic or polymer, may be used to assist with support with the foam material.

In an example, a zipper or other removable connector can be positioned on a side of the garment, e.g., between the front and rear panels or adjacent the front or rear panel. The zipper can assist in securing the garment and releasing the same after exercise. The use and positioning of the connectors may be beneficial to a post-medical procedure wearer of a garment with such connectors.

Optionally, these example garments can be used in a medical context, e.g., post-medical procedure, post-surgical or post mastectomy, to provide adequate support for a wearer after the medical procedure. In an example, the breast cup can have an aperture through which a drainage tube may extend. The tube can provide a fluid connection between the body of the wearer and a drainage container. In an example, the present garment is worn and used with drain container holding system, e.g., the system shown and described in U.S. Pat. No. 6,610,032, which is hereby incorporated by reference for any purpose. However, if U.S. Pat. No. 6,610,032 conflicts with the present explicit disclosure, then the present disclosure controls interpretation.

In various examples, the garment can include a single side entry, e.g., a hook and loop fastener, with the front, back and other side being fixed together in a non-separatable manner, e.g., sewn or using a single fabric construction. This can provide benefits in the medical uses of the present disclosure. The garment can be placed on a bed or gurney with the one side open. A patient can be transferred onto the open garment. The front piece is then brought over the front of the patient and positioned prior to closure. The open edge of the front can be fastened to the open edge of the rear piece. It is believed that this construction may reduce forces on the front of the patient in contrast to a front closure that requires the front to be pulled together more than necessary to close some front closures. This may be beneficial to cardiac patients, e.g., these that have had a procedure that affects the sternum.

Any of the preceding paragraphs in this section can be combined with each other.

The following detailed description includes references to the accompanying drawings, which form a part of the detailed description. The drawings show illustrations in accordance with example embodiments. These example embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

In this document, the terms "a" or "an" are used, as is common in patent documents, to include one or more than one. In this document, the term "or" is used to refer to a nonexclusive "or," such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

FIG. 1A shows a garment 100 (generally in the shape of a brassiere) that includes a right shoulder strap 102 and a left shoulder strap 104 extending from a back panel 106 to a front panel 108. The shoulder straps 102, 104 are adapted to extend over a wearer's shoulders to support and to properly position the garment 100 on the wearer. The shoulder straps 102, 104 are adjustable to position the garment, specifically, the front panel 108, in the vertical direction. The back and front panels 106, 108 are connected to each other to form a continuous covering around the wearer's torso. The front panel 108 is to support the breasts of the wearer in a secure manner during exercise. The front panel 108 includes a formed inner portion, which forms two cups to support a woman's breasts, and an outer portion, which can provide compression to secure the woman's breasts in place. These two portions will be explained in greater detail herein. The back panel 106 is racer back style such that the rear panel is significantly smaller than the front panel 108. When correctly worn by a wearer, the back panel 106 is centered on the mid-sagittal plane of the wearer's body with the bulk of the rear panel resting between the shoulder blades of the wearer. The back panel 106 is to provide support to the front panel 108 and keep the front panel in the proper position for breast support. The front and back panels 108, 106 are connected, e.g., sewn, heat welded or otherwise fixed to each other on sides, e.g., below the arms of the wearer. An elastized band 110 is fixed to the bottom edge of both the front panel 108 and the rear panel 106. The band 110 can be integrally sewn in the body of the panels 106, 108. A left side flap 112 is connected to and cantilevered from a left side of the garment 100 and extends around at least part of the front panel 108 to provide an individual fit for the wearer. A right side flap 114 is connected to and cantilevered from a right side of the garment 100 and extends around at least part of the front panel 108 to provide an individual fit for the wearer. Each of the flaps 112, 114 extend less than half the width of the front panel. The flaps 112, 114 pull the rear and front panels 106, 108 together to reduce the horizontal (here, circumferential) size of the garment.

Figure 1B:
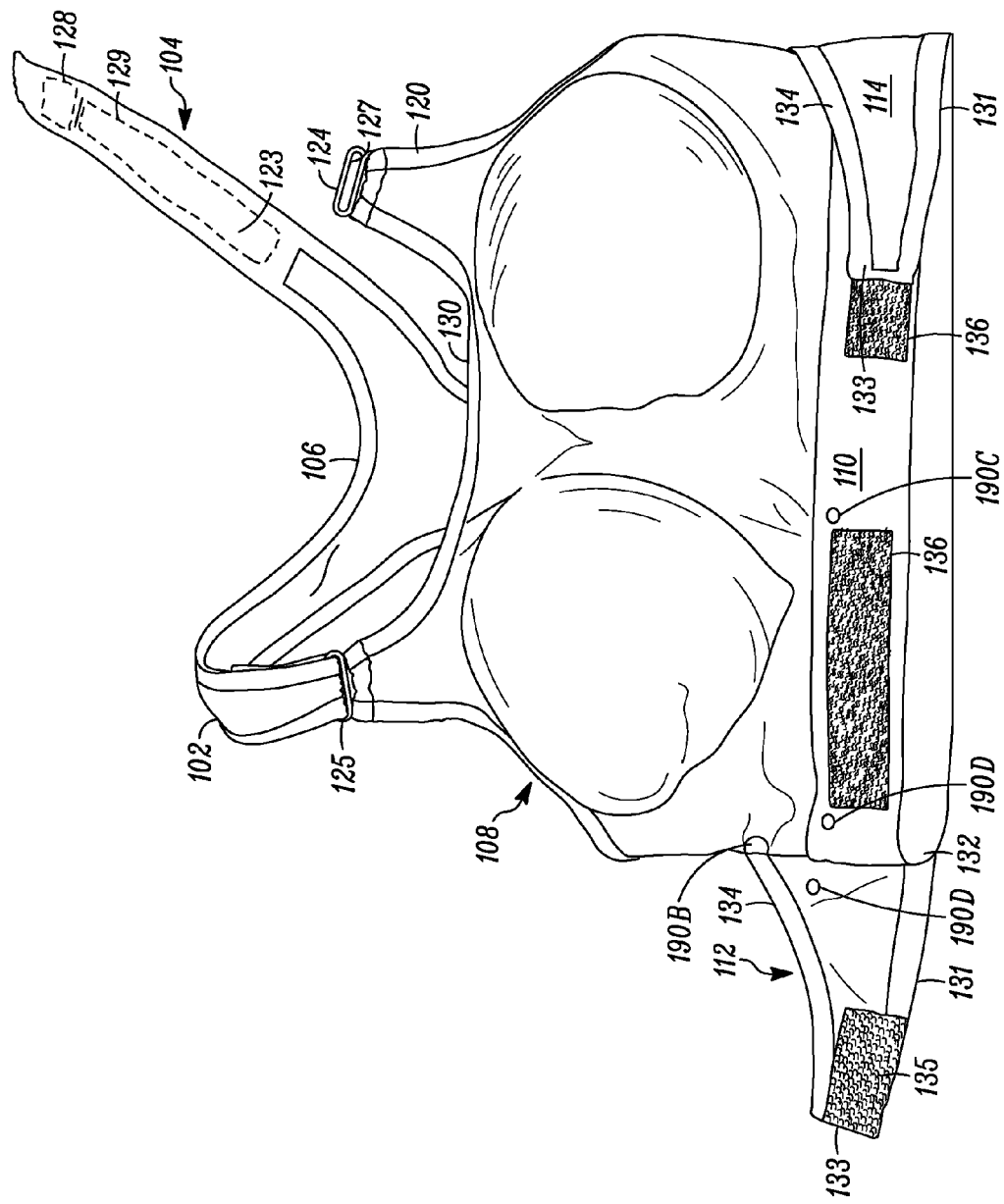
FIG. 1B is a front view of the garment in accordance with an example embodiment.

The front panel 108 can include an aperture 190 through which a drain tube can extend from the wearer's body to outside the garment. In a example, the drainage tube may extend out of the cup between the material of the front panel, cup or side panels and extend down to a drainage collection apparatus. In another example, the aperture 190A is in the cup of the front panel 108. In an example, the aperture 190B (FIG. 1B) is on the side of the front panel 108 generally under the arm of a wearer. The aperture can also include a plurality of apertures positioned at various locations on the front panel. In a further example, the aperture 190C is in the band 110 (FIG. 1B). A drainage tube can also be positioned so that it extends out of the interior of the cup, e.g., over the top or side, to extend down to a drainage bulb that can be attached to the band 110. In another example, the drainage tube aperture is positioned at the side of the garment 100, e.g., under the arm of the wearer.

FIG. 1B shows a front view of the garment 100 with the shoulder strap 104 released from the connector 124 to show the details of the strap 104. It will be recognized the other strap 102 can be the same as strap 104 but a mirror image to comfortably fit on the other side of the wearer's body. Connector 124 includes two elongate apertures. The apertures have two opposed linear sides that receive fabric therein. A front panel aperture is fixed to a left upward extension 126 of the front panel 108. A strap aperture 127 is to receive the free end of the cantilevered strap 104 therein. A same connector 125 connects to the front panel 108 to the right strap 102. Strap 104 includes a hook and loop connector affixed thereto. An example of a hook and loop connector is VELCRO™. The hook part 128 of the connector is affixed to the free end of the strap 104. In an example, the hook part 128 covers substantially the width of the strap 104. The hook part 128 can have a length of about one inch or less. The loop part 129 of connector extends the width of the strap 104 and extends a significant length of the strap 104. The loop part 129 can extend about 6 inches or less. The hook part 128 and the loop part 129 are positioned on the same side of the strap 104. In use, the free end of the strap 104 is inserted through the upper, free, strap aperture 127 and pulled upward to align the hook part 128 with the loop part 129 by folding the strap back onto itself In an example, the strap 104 folds over the front of connector 124 and threads through the aperture 127 from the front to the back. The end of the strap that is through the aperture 127 folds upwardly under the remaining part strap. This can provide a smooth outward appearance to the strap 104 with the free end of the strap 104 tucked under the strap 104. The hook and loop parts are mated together to fix the length of the strap 104. The hook part 128 can be removed from the loop part 129 to adjust the length of the strap 104 so that the front panel is properly aligned for the individual wearing the garment. As a result the front panel 108 can be positioned properly for the individual's body shape in the vertical direction. The two upward extensions on the front panel 108 and the main body form a neckline 130 that is below the top of the back panel and below the neck of the wearer for comfort during exercise.

Shoulder straps 102, 104 can have two configurations. The first configuration is shown as strap 102. The second configuration is shown as strap 104. While shown as two different configurations, it will be understood that the straps 102, 104 can be the same configuration for any individual garment 100. The first and second straps 102, 104 are an elastic fabric, however, the elastic will not stretch to such an extent that the strap allows the front panel to sag. The free end of the strap 104 is threaded under the connector 124 and threaded forwardly through aperture 127 and then folded back on itself The hook and loop connector includes a first part on the forward face of the strap 104 for this type of connection. The folded over part of the strap 104 then on the top of strap part on the wearer's shoulder and not in contact with the wearer's shoulder. However, the strap 104 is shown in FIG. 1B with the connector parts 128 and 129 in the free end, tuck under configuration. The connector parts 128 and 129 would be on the back (nonvisible side in FIG. 1B) of the strap 104 in the free end on top of the strap configuration. In the free end on top configuration of strap 104, the free end of the strap 104 is easily accessed by the wearer and adjustments can easily be made while wearing the garment 100, even while exercising. A cushioning pad 123 can be positioned on each of the straps 102, 104 on the face of the strap whereat the strap comes into contact with the wearer's shoulder. In the strap 104's configuration with the free end of the strap folded over the top of the remaining portion of the strap, the free end will not block part of the cushion 123. Accordingly, the cushion 123 provides a cushion with the body of the wearer over its entire length. In an example, the strap may include a connector to hold a drainage tube in position.

Also shown in FIG. 1B is the right flap 112 in an unconnected position, i.e., it is not affixed to the band 110. The left flap 114 is affixed to the band 110. It will be understood that the flaps 112, 114 can be the same and mirror images of each other on opposite sides of the garment. The flap 112 has a trapezoid shape with a bottom side 131 that is substantially parallel with the bottom side of the band 110. The vertical sides 132, 133 being essentially perpendicular to the bottom side 131. The top side 134 slopes downwardly to the front vertical side 133. In the free position, the flap 112 is only connected to the rear panel 108 at the rear side 132. The rear side 132 has a height that is equal to the height of the rear panel 108 whereat the flap 112 is connected to the rear panel. In another example, the flap 112 is connected to the seam whereat the front panel 108 and the rear panel 106 are connected. In another example, the rear side 133 has a height less than the height of the rear panel 106 at the location whereat the rear side 133 is connected. The rear side 133 will have a height greater than half the height of the rear panel 106, where connected. A connector releasably connects the flap 112 to the band. The connector can be a hook and loop connector. The hook part 135 is fixed to the inner side of the flap 112 adjacent the front side 132. The loop part 136 is fixed to the front face of the band 110. In an example, the hook part 135 and loop part 136 each have a height of about half inch. The hook part 135 has a length of about one and half inch. The loop part 136 can extend across the entire front length of the band 110. In another example, the loop part 136 extends about one-third the length of the band 110. In another example, a break in the loop part 136 is located at the midpoint of the band 110. In use, the wearer grips the flap 112 and pulls the free front end side 133 to align the hook part 135 with the loop part 136. The wearer stretches the flap 112 to create a tension in the fabric of the flap and then fixes the hook and loop parts 135, 136 to connect the free end of the flap to the band 110. The shape of flap 112 distributes the tension from the front side end of the flap to the entire height of the rear panel while pulling the band 110 tighter about the torso of the wearer. Any excess material of at least one of the front panel 108, rear panel 106, and/or band 110 under the flap 112 can fold comfortably at the sides of the wearer. As a result the circumferential size of the band 110 and the garment 100 as a whole can be adjusted to fit the wearer's torso and the comfort level of the wearer. The circumferential size and tension of the garment 100 are adjustable such that the garment can be individualized for any wearer.

Figure 2:
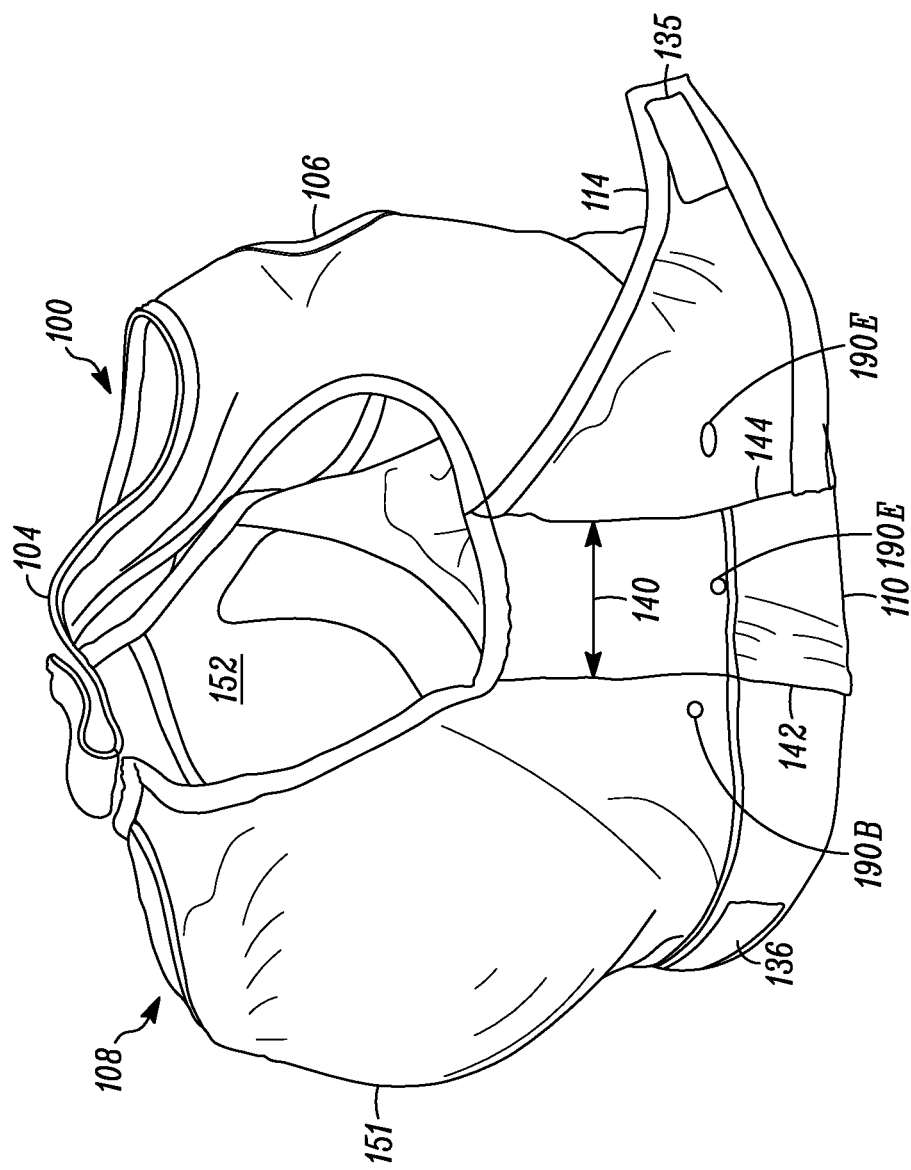
FIG. 2 is a side view of the garment in accordance with an example embodiment.

An aperture 190D can also be aligned with the flap 112. Aperture 190D can extend through the front panel or through the band at a location where it would be at least partially covered or completely covered by the flap 112 when the garment is worn. The aperture 190D can provide a through hole so that a drain tube can extend from the wearer's body to exterior the garment 100. While FIG. 2 shows a side view of the garment 100 with the flap 114 free from connection to the front of the band 110 to show the side portion 140 of the garment 100 that can be pulled together to reduce the circumference of the garment 100. The width of the side portion 140 is measured from the seam 142, where the back panel 106 is connected to the front panel 108, and the seam 144, where the flap is fixed to the rear panel 106. It will be further recognized that the loop part 136 extends far enough to the other side that the flap 114 can move its seam 144 to seam 142 with the hook part 135 fully engage the loop part 136 on the front of the band 110.

The front panel 108 includes a fabric cover 151 that extends the entire size of the front panel. Fabric cover 151 is at least one layer of a stretchable, vertically and horizontally, fabric that can provide tension and compression to the front of the wearer. The stretchable fabric can be a knit material that can include LYCRA™, spandex, or other synthetic stretchable polymer. In an example, the resilient stretchable material is up to 10% of the content of the fabric. Other wicking material can be used in the fabric cover, e.g., COOLMAX™. Cover 151 extends the entire extent of the front panel and it connects to the rear panel 106. Cup assembly 152 is positioned beneath the cover 151 and is partially visible in FIG. 2. The cup assembly 152 is not visible in FIGS. 1A and 1B as the cover 151 completely covers the cup assembly 152 but the cup assembly 153 is form holding (e.g., semi-rigid). Hence, the cup assembly 152 gives a shape to the front panel 108 which would not exist due to the fabric cover alone. The cup assembly 152 defines two distinct cups 153, 154 (see, FIGS. 3 and 4 for a better view of the cups) for receiving the breasts of a wearer. The cup assembly 152 can support and secure the breasts in place, particularly when the wearer as a larger cup size, and can help reduce the single breast look when both breasts are compressed in a traditional sports bra or medical compression bra. The two individual cups 153, 154 can individually encapsulate the wearer's breasts.

Apertures, e.g., 190B or 190E, can be positioned on the side of the garment 100. An aperture 190E is in a side of the band 110 and must extend through the flap 112. However, as the flap 112 may not always be in the same position relative to side part of the garment 100, the aperture in the flap may be vertically aligned and the same vertical dimension as the aperture in the side of the front panel (or rear panel depending on the construction). However, the aperture in flap 112 may be elongate in the horizontal direction to account for the operation of the flap 112 to alter the width of the garment in direction 140.

Figure 3:
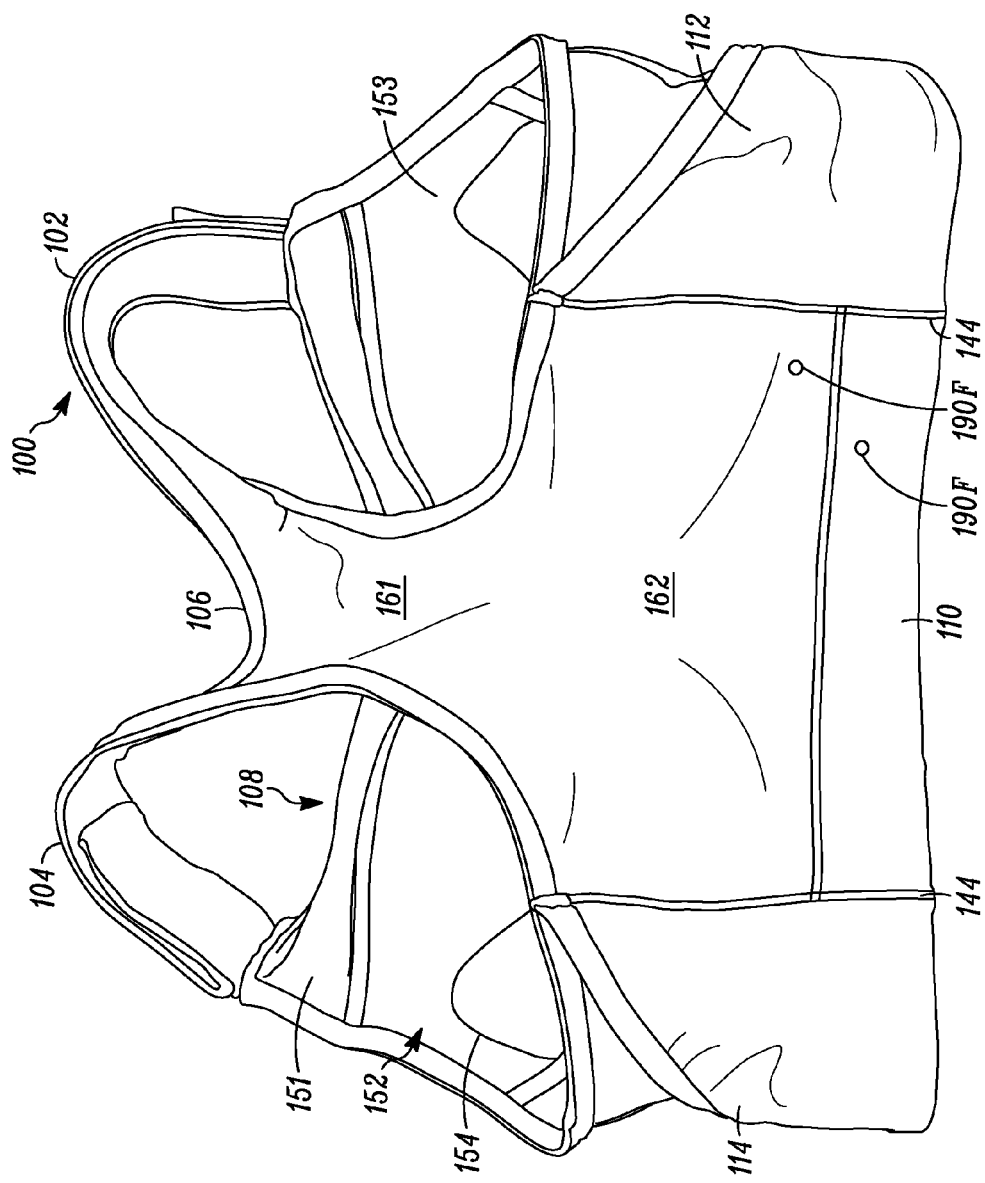
FIG. 3 is a rear view of the garment in accordance with an example embodiment.

FIG. 3 shows a rear view of the garment 100 including the rear band portion 110B, which can have a stronger elastic strength than the remainder of the band. The rear panel 106 includes a narrow upper portion 161 that can seamlessly transition into the straps 104, 106. Upper portion 161 is sized such that it essentially lies between the scapulae of the wearer and not interfere or chaff the user during exercise. The rear panel 106 includes a lower portion 162, which can be an integral fabric with the upper portion 161. The lower portion 162 has a height that extends from essentially beneath the wearer's scapulae and to essentially beneath the circumferential line beneath the wearer's breasts. Accordingly, the shape of the upper portion 161, the lower portion 162, straps 102, 104, and the top part of the front panel 108 to not interfere with freedom of movement of the arms and shoulders of the wearer. In an example, the rear panel 106 or rear part of the band 110 can include an aperture 190F through which a drain tube can extend.

Figure 4:
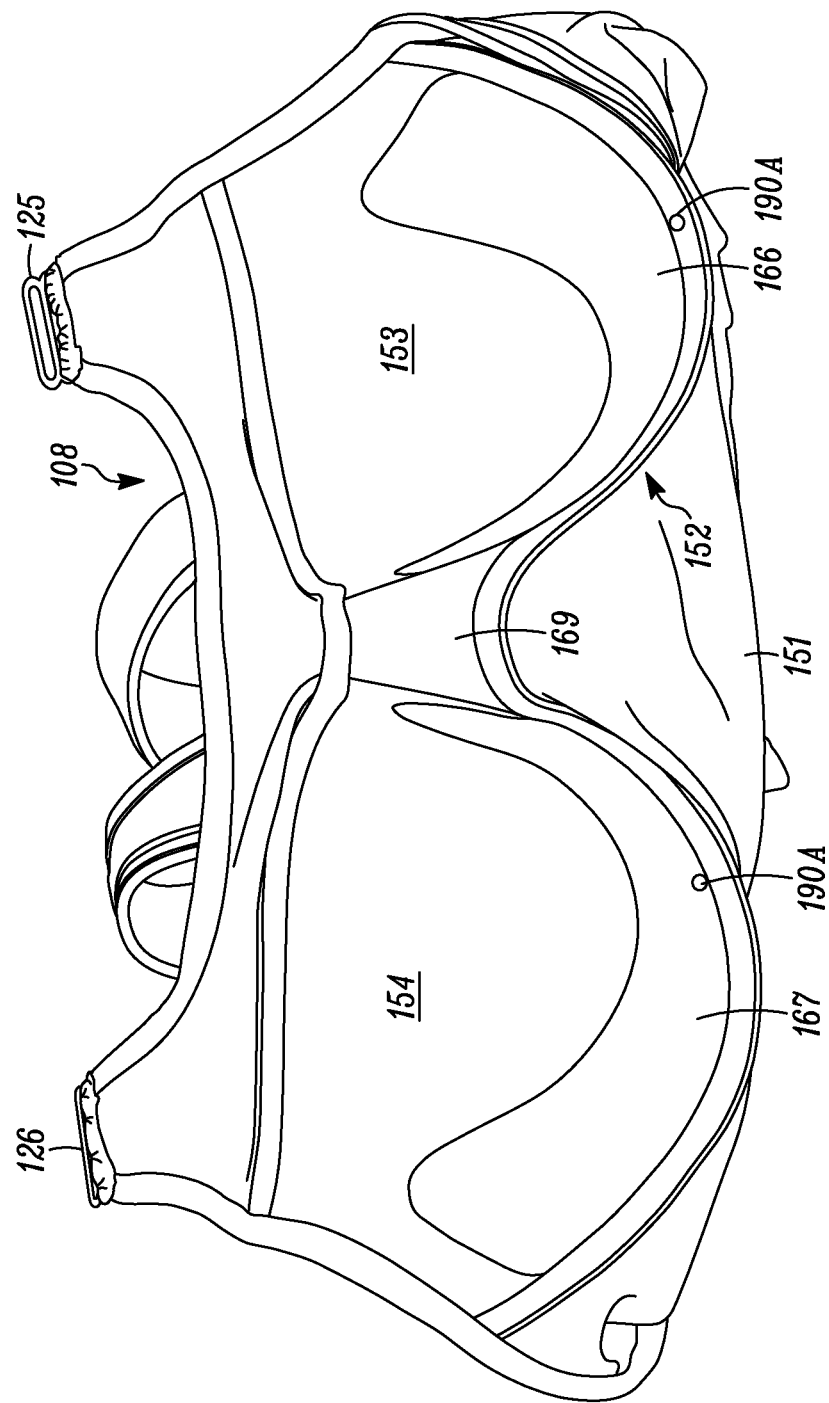
FIG. 4 is an interior view of the front of the garment in accordance with an example embodiment.

FIG. 4 shows a rear view of the front panel 108 including the cover 151 and the cup assembly 152, i.e., the rear panel is removed to more clearly show the cup assembly 152. The right and left cups 153 and 154 can be sized to fit a woman's breast size and individually encapsulate a wearer's breast. Thus, the inventor's of the present invention have found that a cup, e.g., A, B, C, D, DD, etc. that matches a wearer's breast size with a compressive cover, i.e., 151, provides a more comfortable fit and secures the breasts during exercise. However, larger cup sizes may require more support. An under support 166, 167 is positioned along the bottom arcuate side of the cups 153, 154, respectively. The under support 166, 167 is positioned such that it extends under the wearer's breasts to provide further support. In an example, the under support 166 or 167 is a foam insert within the respective cup. The foam can have a density. In an example, the under supports 166, 167 are a gel with the cup. In an example, the under supports 166, 167 are a pliable polymer material that provides support without causing pressure points on the wearer. In a further example, the under support 166, 167 can be an underwire if the underwire is coated or covered such that it does not provide pressure points on the wearer. The foam insert under support 166, 167 create a thicker portion of the respective cup that the remainder of the cup. The under support extends inwardly into the concave portion of the cup such the outer portion of the cup is smooth to provide an attractive, smooth appearance for the wearer.

The cup assembly 152 includes a bridge 169 is positioned between the cups 153, 154. The bridge 169 has the less height as compared to the remainder of the cup assembly. The bridge is essentially flat and narrower at the top than at the bottom. The inner ends of the under supports 166, 167 end adjacent the bridge 169. The bridge 169 is a semi-rigid fabric, in an example. Semi-rigid means that the bridge will hold its shape and hold the cups in position unless a significant force is applied to the bridge. A significant force may be greater than forces applied to a brassiere while it is being conventionally worn on the body of a wearer. The bridge 169 acts to hold the cups 153, 154 laterally in place. The bridge 169 is rigid to such an extent that it does not allow the cups 153, 154 to move laterally relative to each other, yet allows the cups to move forward and rearward. As a result, the cups 153, 154 individually encapsulate the wearer's breasts prior to compression by the outer fabric cover 151 with the bridge 169 holding the two cups 153, 154 in place relative to each other.

Figure 5:
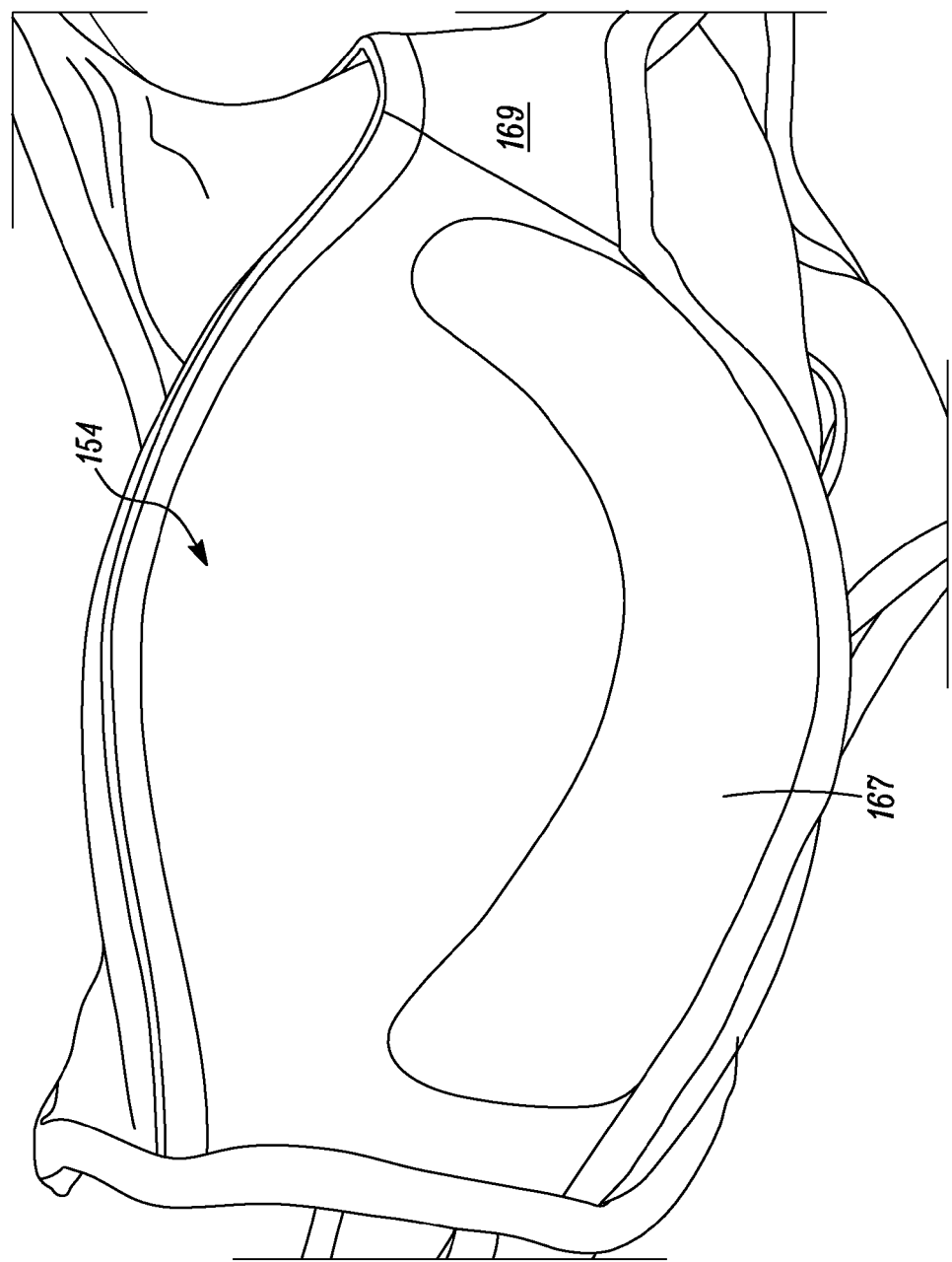
FIG. 5 is an enlarged, interior view of the garment in accordance with an example embodiment.

FIG. 5 shows an enlarged view of the cup 154 with the under support 167 and the bridge 169. The cup 154 can help lift the breast therein by the under support 167 and encloses the breast tissue therein. The outer fabric cover can then compress against the cup 154, which is holding the breast. Traditional sports bras do not provide a cup that lifts, encapsulates, and then compresses the breasts as the present invention can. Moreover, traditional sports bras are nor designed to be post-surgical garments that may be used with a drainage collection apparatus.

Figure 6:
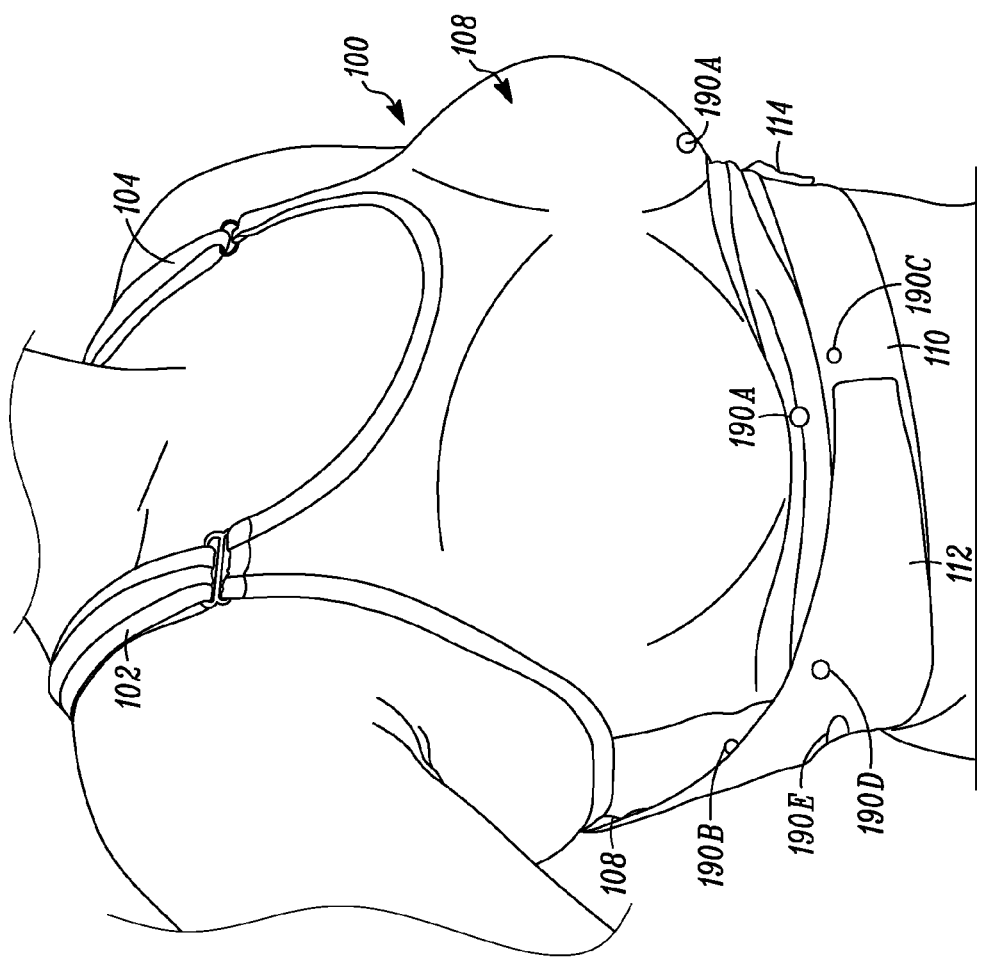
FIG. 6 is a view of the garment being worn during use in accordance with an example embodiment.

FIG. 6 shows the exercise garment 100 being worn during use with the shoulder straps 102, 104 over the shoulders of the wearer with the wearer's breasts being held (lifted, encapsulated and then compressed) in the front panel 108. The side flaps 112, 114 assist in tightening the garment around the wearer's torso.

Figure 7:
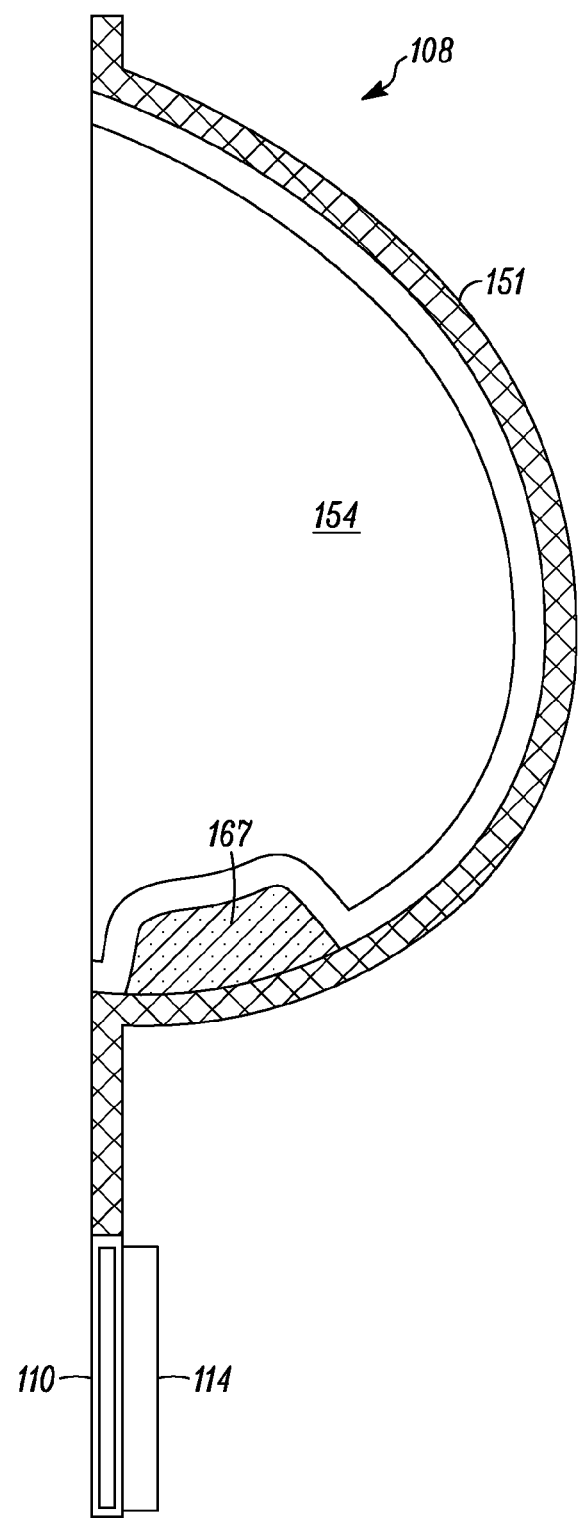
FIG. 7 is a cross-sectional view taken generally along line 7-7 of FIG. 1 in accordance with an example embodiment.

FIG. 7 is a cross-sectional view taken generally along line 7-7 of FIG. 1 of the garment 100. The front panel 108 includes the front cover 151 overlying the entire cup 154. The under support 167 is positioned between the cup material and the cover 151 material. The flap 114 is affixed to the band 110 beneath the cup 154.

Figure 8:
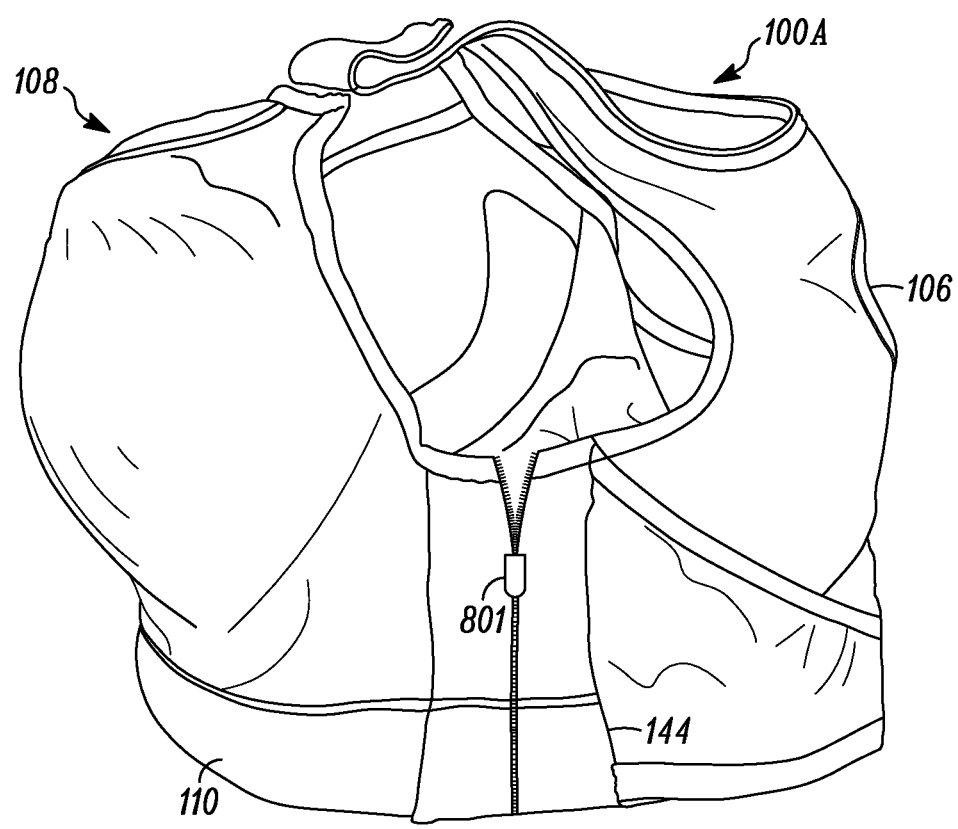
FIG. 8 is a side view of the garment in accordance with an example embodiment.

FIG. 8 is a side views of a garment 100A similar to the side view of garment 100 described above. Garment 100A is similar to garment 100 in that it has a front panel 108 and a rear panel 106. Garment 100A includes a vertical closure 801 that releasably connects the front and rear panels 108, 106 together. In an example the closure 801 is a zipper. In other embodiment, the closure 801 can be a laced tie or hook and loop fastener. The closure 801 can extend the entire height of the side of the garment 100A.

Figure 9:
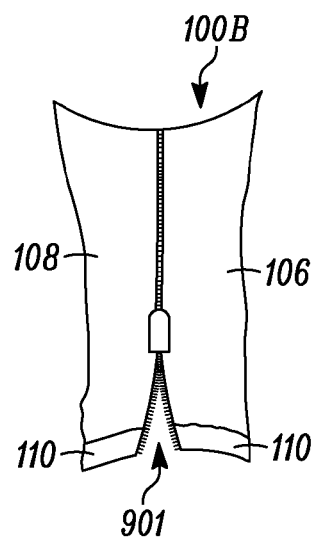
FIG. 9 is a further side view of the garment in accordance with an example embodiment.

FIG. 9 shows a partial side view of a garment 100B where the closure 901 does not release the entire height of the garment side. The closure 901 releases from the bottom to release the tension on the garment such that the wearer can more easily disrobe. In an example, the bottom band 110 is elastic and expands about one inch to the torso circumference of the wearer for a snug fit. However, during exercise, the garment becomes wet with perspiration and may be difficult to remove. Here, the wearer releases the closure 801 to release the tension of the band or the body of the garment to make the garment easier to remove.

Figure 10:
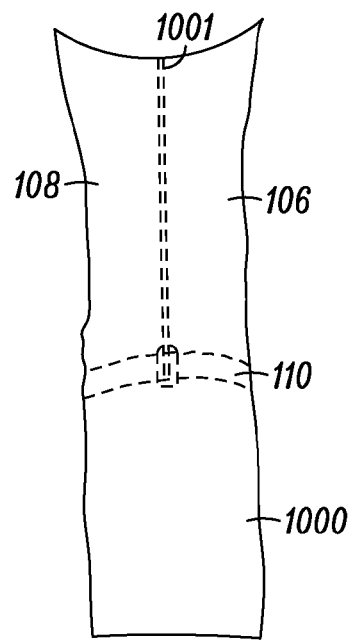
FIG. 10 is a side view of a garment in accordance with an example embodiment.

FIG. 10 shows a partial side view of a garment 100C, which includes a shirt 1000 that can be connected to the front panel 108 and the rear panel 106. In an example, the shirt 1000 is constructed as a single fabric. Otherwise the front and rear panels 108, 106 can be the same as those described herein. The shirt 1000 extends downwardly from the band 110 to cover more of the wearer's torso. A closure device 1001 is provided to allow the garment 100C to be loosened and tightened on the wearer's body. For example, the closure 1001 is shown under the outer fabric. The closure acts to hold the front panel 108 and rear panel 106 in place to support the wearer's breasts. In an example, the closure device 1001 is a zipper defining a closed position with slider at the bottom beneath or at the band 110. In an example, the closed position of the device 1001 is at the top of the garment 100C. While shown as under the outer layer of the shirt 1000, it is within the scope of an embodiment to position the closure 1001 at the outside of the shirt 1000.

In an example, the front panel 108 includes a cup assembly (not shown in FIG. 10) as described herein. Other cup assemblies can be used with this shirt version of the present garment 100C. The cup assemblies for use with garment 100C can be a flexible, limp fabric that defines a cup as opposed to the semi-rigid, more supportive cup assembly 152 described above. This fabric cup assembly can be in two separate parts at each cup location. These separate parts are connected to the outer, compressive layer of the front panel 108. In an example, the fabric cup assembly is a wicking or mesh fabric. The shirt-like garment 100C can also be used with a wound drainage collection apparatus.

Figure 11:
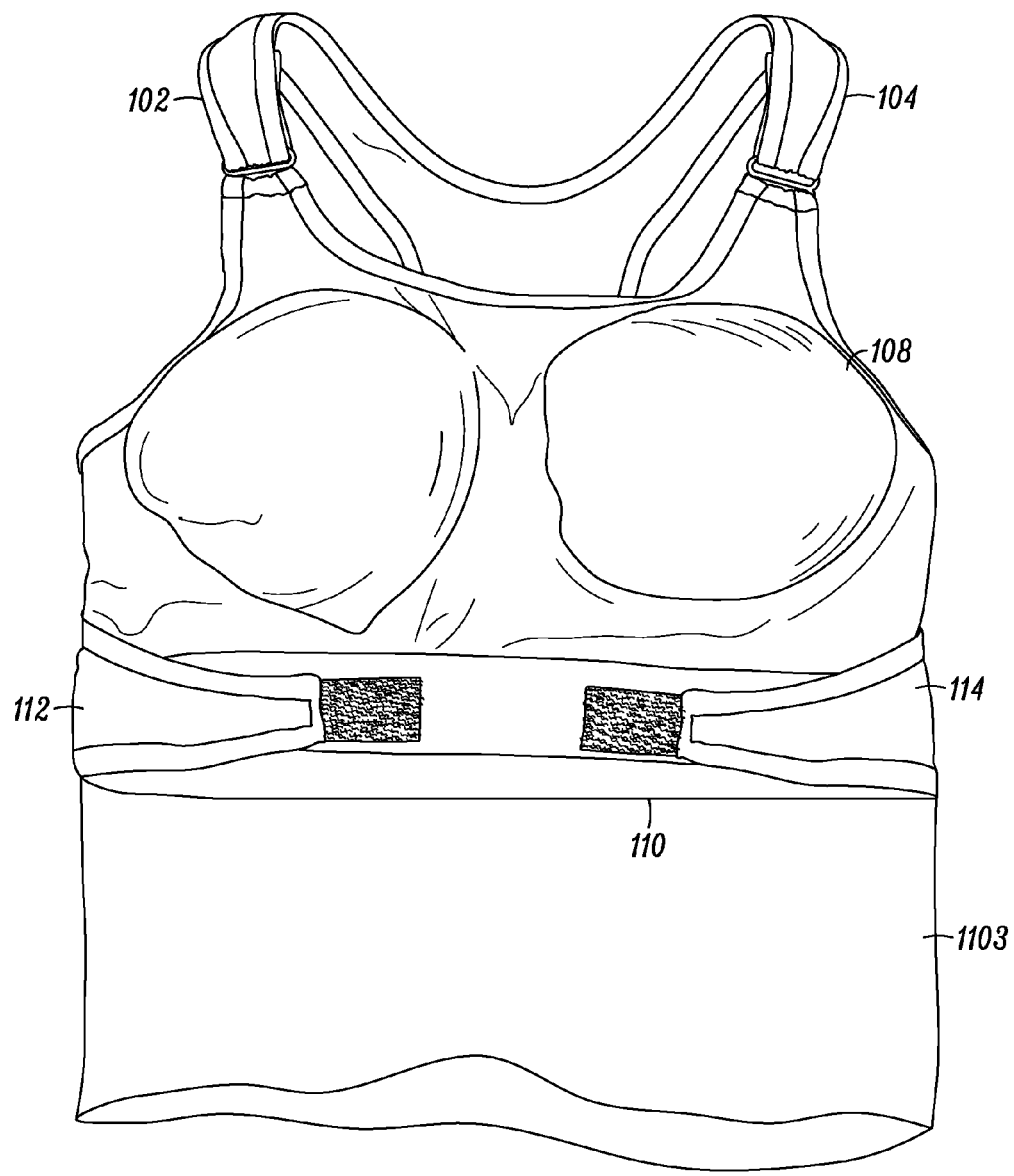
FIG. 11 is a front view of a garment in accordance with an example embodiment.

FIG. 11 shows a front view of a garment 100D, which includes a shirt extension 1103 that extends downwardly from band 110 to cover more of the torso and the abdomen of the wearer. Garment 100D includes the front panel 108 and tightening flaps 112, 114 as described herein. The straps 102, 104 can also be the same as those described herein. This shirt garment 100D can further be modified to replace the flaps 112, 114 with the closures 801, 901, or 1001, which would operate as described herein. The shirt-like garment 100D can also be used with a wound drainage collection apparatus.

In a further example, garment 100D can include the side closures 901, 1001 on the sides thereof. Adding the side closures 901, 1001 to the garment 100D provides additional ease of use, e.g., putting on and taking off the garment 100D.

Figure 12:
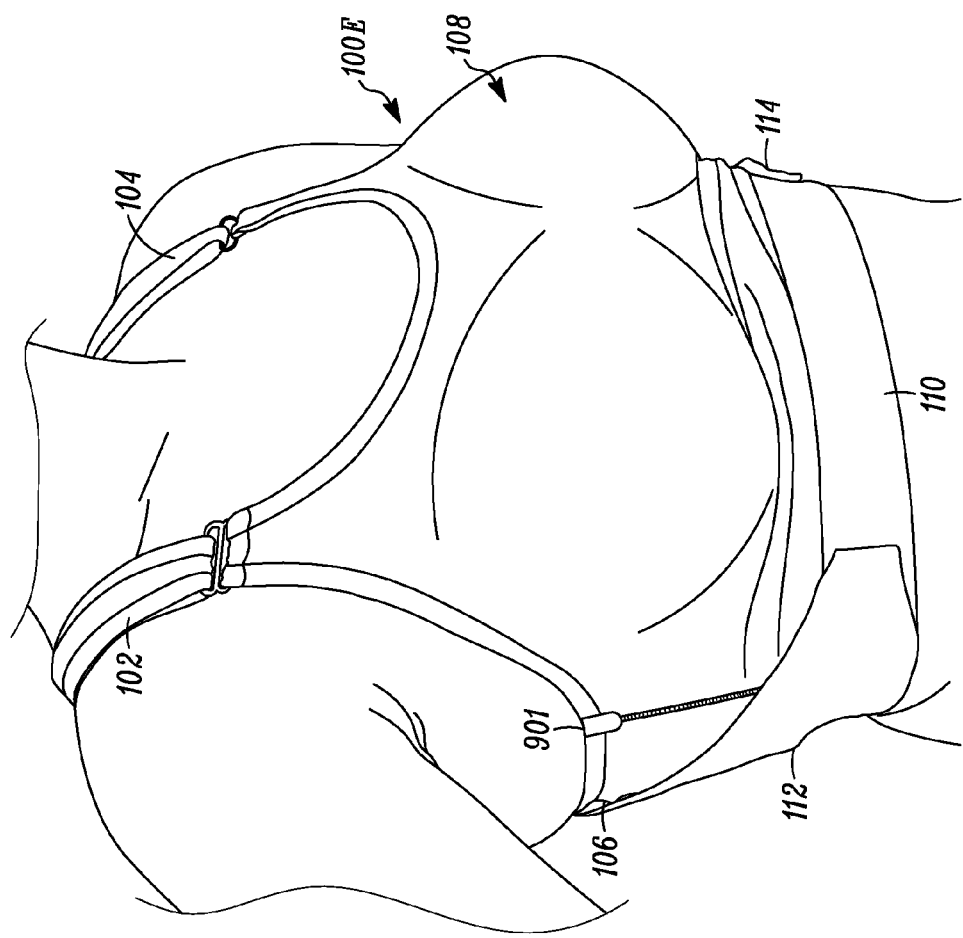
FIG. 12 is a view of the garment being worn during use in accordance with an example embodiment.

FIG. 12 shows a view of the garment 100E that includes the same features as with regard to FIGS. 1-6 as well as a side closure 901, which can be the same as the closures shown in FIGS. 9-10. Closure 901 is shown in the closed position. If the closure 901 is opened, then the front panel 108 and the rear panel 106 on the side of the wearer can move apart from each other. This will ease the ability to take off and put on the garment 100E. In the illustrated example, the closure 901 is a zipper can extend beneath the flap 112. In an example, the closure 901 is only on one side of the garment 100E. In an example, a closure is on each side of the garment. The closure 901 can extend all the way through the garment 100E so that the front panel 108 and rear panel 106 are completely separated. The closure 901, in an example, only extends partway down the side of the garment. It will further be recognized that the closure 901 can be positioned as shown in FIG. 9 and closed when at the bottom of the garment 100E. When the closure is a zipper, it can have its slider under the flap when the garment is worn.

The rear panel 106, part of the front panel 108, straps 102, 104, flaps 112, 114, i.e., structures except for the cup assembly 152, of the garment can be constructed of at least one of stretchable polymer, woven fabric that provides both vertical and horizontal stretch. In an example, the fabric used for the garment can be up to ten percent spandex and the remainder polyester. In an example, spandex is eight percent. In an example, spandex is sixteen percent. In some embodiments, spandex can be up to about 20%, +/−2%. The percent can be measured by weight or by thread count. Examples of fabrics include COOLMAX™ material by Invista North America of Wilmington Del., DRYLAYER™ material by Russell Brands of Alexander City Ala., SUPPLEX™ or LYCRA™ material by Invista North America of Wilmington Del., all of which provides stretch, support, breathability for the skin and reinforcement of the garment 100. Moreover, the garment structures described herein can further be fabricated as multiple pieces that are then joined together to provide the structures described herein.

Rear panel 106 is described as a racer back construction. It will be recognized that other rear panel styles can be used in the present invention. In an example, the rear panel 106 can be a full back panel that extends to cover the back of the wearer, including over the scapulae of the wearer. In a further example, the rear panel 106 can have a profile that is substantially similar to the front panel as shown herein.

It will further be within the scope of the present disclosure to provide the apertures 190A-190F in any of the examples shown in FIGS. 7-12. The apertures are optional as a drainage tube may be run out of the top of the garment 100, e.g., the top of the cup assembly. In some examples, there are no apertures and the drainage tube extends out of an open space in the garment to a drainage collection apparatus.

While many of the above examples describe hook and loop connectors in certain configurations where the hook part and the loop part are on the certain structures. It will be understood that the hook and loop parts could be reversed and positioned in the other structure. The hook and loop connector can be VELCRO™.

The present inventor has further determined that exercise bras must also have an attractive appearance and comfort for them to be accepted by women. The present garments can be made in varying chest and breast cup sizes while providing adequate support for women engaging in exercise and sports. It is known that exercise and sports can result in negative impact on the breast tissue if not adequately supported. The design of the present garment provides much greater comfort to the wearer's breasts than current sports bras. This increased comfort can result in the garment being worn longer than conventional sports bras, which can result in the wearer exercising for longer periods of time and more frequently as soreness due to inadequate support. The garment is individually adjustable in both vertical and horizontal directions to provide an individual fit for the wearer as women's bodies are all different. Moreover, if a woman loses weight over time or has gained weight, then the garment can be adjusted accordingly to continue to fit the woman properly. Similar fit concerns are of concern in post-medical procedure garments. The presently described garment may be of use to women following a medical procedure.

The present inventor has unexpectedly recognized the need to improve women's exercise apparel, and post-medical procedure garments, by providing a garment that individually lifts a woman's breasts, individually encapsulates each breast in an individual cup, and then compresses the breasts to hold then in place while exercising. The present garment allows a woman to present a more natural looking profile while maintaining proper support. It is further believed that providing a natural profile will help the wearer look better and feel better about herself, and hence be more likely to exercise. In the area of post medical procedure garments, a properly fitting garment is more likely to be worn by a patient and may assist in proper recovery.

Some women today have a significant investment in breast reconstruction or augmentation. The present garment can protect these investments and help reduce the likelihood of addition corrective surgery by properly supporting the breast during exercise. It has been reported that a woman's breast can move up to 21 cm. during exercise and hence it is important to properly support and restrict movement during exercise.

It will further be recognized that the garment can include pockets to carry items, such as music players or medical readers. Such pockets may be on the cup, front panel, straps, back panel, or side panels.

Thus, exercise garments, such as bras, support shirts, and tankinis, and methods of their use have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

In an example embodiment, a medical garment includes a rear panel and a front panel connected to the rear panel. The medical garment can be a post-surgical garment, post-medical procedure garment, a garment to be worn while undergoing a medical procedure or other applications where a fluid connection to a wearer's body may be desired for an extended period of time. The front panel includes an elastic, outer cover fabric and a cup assembly to receive the breasts of the wearer. The cup assembly defines two cups that are joined by a bridge. The cup assembly encapsulates the wearer's breasts in an essentially non-stretchable fabric. The cover fabric can be elastic and can compress against the cup assembly to secure the wearer's breasts in place. An elastic band is positioned beneath the cup assembly to secure the garment on the torso of the wearer. Shoulder straps extend from the front panel to the rear panel. The garment further includes a circumferential tightening structure to tighten the circumference of the garment around the torso of the user. The circumferential tightening structure can engage the front of elastic band or the front panel to pull the front and rear panels together to tighten the garment or reduce the circumferential size of the garment.

The shoulder straps can be adjustable in length to position the front panel vertically. To be adjustable the shoulder straps are cantilevered (e.g., fixed to the rear panel) from the rear panel and releasably connect to the front panel. The free ends of both the shoulder straps can lie over a portion of the respective first strap and second strap and secure thereto.

In an example, the circumferential tightening structure includes at least one side flap that in a first, free position is connected to only one of the front panel and the rear panel and in a second, tensioning position has another end that connects to the other of the front panel and rear panel. Flaps can be positioned on both sides of the garment. The rear sides of the flaps can be fixedly connected to the rear panel and extend essentially the height of the rear panel. The flaps can include a narrower end that is adapted to wrap around to the front panel and engage at least one of the front panel and the band to tension the garment around the torso of the wearer.

The elastic band is positioned on the bottom of the garment and can have one part of a first hook and loop connector. The flaps can include the other part of the first hook and loop connector such that first hook and loop connector releasably joins the flaps to the front of the band. The connector can release tension between the front panel and rear panel to assist in removing the garment from the wearer.

In an example, a fluid storage device is removably attached to the circumferential tightening structure. A second hook and loop connector connects the fluid storage device to the circumferential tightening structure. A loop part of the second connector is attached to at least one flap and a hook part of the connector is attached to the fluid storage device. The fluid storage device has a cap with an inlet nozzle. At least one aperture extends through the cup assembly and a drainage tube is positioned to extend through the aperture and be connected to the inlet nozzle. In an example, the fluid storage device is a wound drainage collection apparatus.

In another example, a fluid storage device is removably attached to the elastic band. A second hook and loop connector connects the fluid storage device to the elastic band. A loop part of the second connector is attached to the elastic band and a hook part of the connector is attached to the fluid storage device. The fluid storage device has a cap with an inlet nozzle. At least one aperture extends through the cup assembly and a drainage tube is positioned to extend through the aperture and be connected to the inlet nozzle.

In an additional example, a fluid storage device is removably attached to the circumferential tightening structure. A hook and loop belt connects the fluid storage device to the circumferential tightening structure. A hook and loop belt is attached to at least one flap and a retaining band is attached to the fluid storage device. The fluid storage device has a cap with an inlet nozzle. At least one aperture extends through the cup assembly and a drainage tube is positioned to extend through the aperture and be connected to the inlet nozzle.

In one more example, a fluid storage device is removably attached to the surgical garment. A skirt extends below the elastic band. One or more pockets are located in the skirt. The fluid storage device can be inserted into and removed from the pocket. The fluid storage device has a cap with an inlet nozzle. At least one aperture extends through the cup assembly and a drainage tube is positioned to extend through the aperture and be connected to the inlet nozzle.

FIG. 13A shows a post-surgical garment or a medical (e.g., a mastectomy, lumpectomy, lymphadenectomy, cardiac surgery, heart surgery, lung surgery, other torso surgeries, etc.) garment 200 that includes a right shoulder strap 102 and a left shoulder strap 104 extending from a back panel 106 to a front panel 108. The shoulder straps 102, 104 are adapted to extend over a wearer's shoulders to support and to properly position the garment 200 on the wearer. The shoulder straps 102, 104 are adjustable to position the garment, specifically, the front panel 108, in the vertical direction. The back and front panels 106, 108 are connected to each other to form a continuous covering around the wearer's torso. The front panel 108 is to support the breasts of the wearer in a secure manner during exercise. The front panel 108 includes a formed inner portion, which forms two cups to support a woman's breasts, and an outer portion, which can provide compression to secure the woman's breasts in place. These two portions will be explained in greater detail herein. The back panel 106 is racer back style such that the rear panel is significantly smaller than the front panel 108. When correctly worn by a wearer, the back panel 106 is centered on the mid-sagittal plane of the wearer's body with the bulk of the rear panel resting between the shoulder blades of the wearer. The back panel 106 is to provide support to the front panel 108 and keep the front panel in the proper position for breast support. The front and back panels 108, 106 are connected, e.g., sewn, heat welded or otherwise fixed to each other on sides, e.g., below the arms of the wearer.

An elastized band 110 is fixed to the bottom edge of both the front panel 108 and the rear panel 106. The band 110 can be integrally sewn in the body of the panels 106, 108. A left side flap 112 is connected to and cantilevered from a left side of the garment 200 and extends around at least part of the front panel 108 to provide an individual fit for the wearer. Left side flap 112 has an outer surface 112A and an inner surface 112B. A right side flap 114 is connected to and cantilevered from a right side of the garment 100 and extends around at least part of the front panel 108 to provide an individual fit for the wearer. Right side flap 114 has an outer surface 114A and an inner surface 114B (seen in FIG. 14). Each of the flaps 112, 114 extend less than half the width of the front panel. The flaps 112, 114 and rear and front panels 106, 108 and band 110 form a circumferential tensioning or tightening structure 208. The circumferential tightening structure 208 of flaps 112, 114 pull the rear and front panels 106, 108 together to reduce the horizontal (here, circumferential) size of the garment and tension the garment about the wearer.

A drainage fluid storage or holding device or assembly 250 has a container, bag or bottle 252 that is at least partially transparent so that a user may view the contents of container 252. Container, bag or bottle 252 can be formed from a flexible material such as plastic. In one embodiment, container 252 can be collapsible such that it can be positioned close to the body of the wearer and not excessively protrude. A cap 254 is releasably attached to container 252. Cap 254 can be attached by threads or may be press fit onto housing 252. In one embodiment, cap 254 may be permanently attached to housing 252. Cap 254 has a tapered inlet nozzle 256 and an outlet nozzle 258. A plug 259 can be inserted into outlet nozzle 258 in order to seal outlet nozzle 258. Plug 259 is retained to cap 254 by a tether 257. Drainage tube 260 has ends 262 and 264. Tube end 262 can be connected to inlet nozzle 256 by press fitting end 262 over inlet nozzle 256. Inlet nozzle 256 can have circumferential ribs to retain end 262. Drainage tube end 264 is adapted to be implanted at a surgical site. Apertures 204 extend through front panel 108. Drainage tube end 264 can be inserted through an aperture 204 and continue to the surgical site. In an example, apertures 204 are round. In another example, apertures 204 are elongated and form a slot. In an additional example, apertures 204 take the form of a slit in front panel 108. In one example, apertures 204 are located at the bottom of the breast cups. In another example, apertures 204 are located at the sides of the breast cups.

A releasable fastener or connector 270 can be used to attach drainage fluid storage or holding assembly 250 to medical garment 200. Connector 270 can be a hook and loop connector. Connector 270 includes a generally planar hook tab or member 271 and loop strips 210. Hook tab or member 271 can have hooks on one side or both sides. Hook tab or member 271 is connected to cap 254 by an arm 272. In one embodiment, hook member 271 and arm 272 are injection molded directly with cap 254 from a plastic material. In another embodiment, hook member 271, arm 272 and retention loop 274 are formed from a fabric material. Retention loop 274 can be held to container 252 by cap 254.

Loop strips 210 are attached or fixed to the front of medical garment 200. A pair of loop strips 210 are attached to the outer side or surface 112A of flap 112. Another pair of loop strips 210 are attached to the outer side or surface 114A of flap 114. Loop strips 210 can be attached to outer surfaces 112A and 114A by any suitable method such as sewing or using an adhesive. Drainage fluid storage or holding assembly 250 can be attached and detached from flaps 112 and 114 using hook and loop connectors 270. In an example, loop strips 210 each have a height of about half inch and a length of about one and half inch. In another example, loop strips 210 each have a height of about half inch and extend across the length of each of outer sides or surfaces 112A and 114A.

Figure 13B:
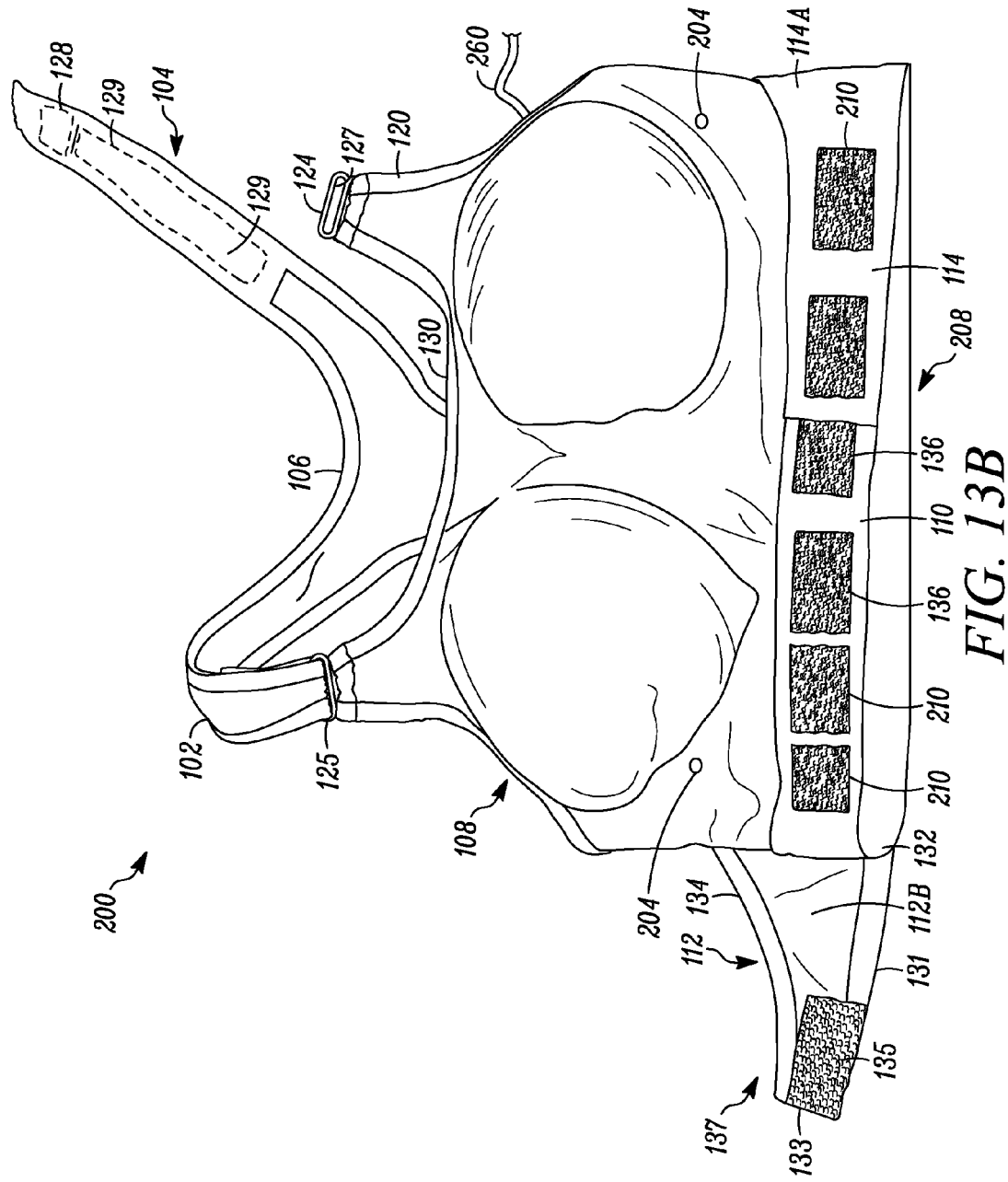
FIG. 13B is another front view of the medical garment in accordance with an example embodiment.

FIG. 13B illustrates a front view of the medical garment 200 with the shoulder strap 104 released from the connector 124 to show the details of the strap 104. It will be recognized the other strap 102 can be the same as strap 104 but a mirror image to comfortably fit on the other side of the wearer's body. Connector 124 includes two elongate apertures. The apertures have two opposed linear sides that receive fabric therein. A front panel aperture is fixed to a left upward extension 120 of the front panel 108. A strap aperture 127 is to receive the free end of the cantilevered strap 104 therein. A same connector 125 connects to the front panel 108 to the right strap 102. Strap 104 includes a hook and loop connector affixed thereto. An example of a hook and loop connector is VELCRO™. The hook part 128 of the connector is affixed to the free end of the strap 104. In an example, the hook part 128 covers substantially the width of the strap 104. The hook part 128 can have a length of about one inch or less. The loop part 129 of connector extends the width of the strap 104 and extends a significant length of the strap 104. The loop part 129 can extend about 6 inches or less. The hook part 128 and the loop part 129 are positioned on the same side of the strap 104. In use, the free end of the strap 104 is inserted through the upper, free, strap aperture 127 and pulled upward to align the hook part 128 with the loop part 129 by folding the strap back onto itself. In an example, the strap 104 folds over the front of connector 124 and threads through the aperture 127 from the front to the back. The end of the strap that is through the aperture 127 folds upwardly under the remaining part strap. This can provide a smooth outward appearance to the strap 104 with the free end of the strap 104 tucked under the strap 104. The hook and loop parts are mated together to fix the length of the strap 104. The hook part 128 can be removed from the loop part 129 to adjust the length of the strap 104 so that the front panel is properly aligned for the individual wearing the garment. As a result the front panel 108 can be positioned properly for the individual's body shape in the vertical direction. The two upward extensions on the front panel 108 and the main body form a neckline 130 that is below the top of the back panel and below the neck of the wearer for comfort.

Shoulder straps 102, 104 can have two configurations. The first configuration is shown as strap 102. The second configuration is shown as strap 104. While shown as two different configurations, it will be understood that the straps 102, 104 can be the same configuration for any individual garment 200. The first and second straps 102, 104 are an elastic fabric, however, the elastic will not stretch to such an extent that the strap allows the front panel to sag. The free end of the strap 104 is threaded under the connector 124 and threaded forwardly through aperture 127 and then folded back on itself. The hook and loop connector includes a first part on the forward face of the strap 104 for this type of connection. The folded over part of the strap 104 is then on the top of strap part on the wearer's shoulder and not in contact with the wearer's shoulder. However, the strap 104 is shown in FIG. 13B with the connector parts 128 and 129 in the free end, tuck under configuration. The connector parts 128 and 129 would be on the back (nonvisible side in FIG. 13B) of the strap 104 in the free end on top of the strap configuration. In the free end on top configuration of strap 104, the free end of the strap 104 is easily accessed by the wearer and adjustments can easily be made while wearing the garment 200. A cushioning pad 123 can be positioned on each of the straps 102, 104 on the face of the strap whereat the strap comes into contact with the wearer's shoulder. In the strap 104's configuration with the free end of the strap folded over the top of the remaining portion of the strap, the free end will not block part of the cushion 123. Accordingly, the cushion 123 provides a cushion with the body of the wearer over its entire length.

Also shown in FIG. 13B is the right flap 112 in an unconnected position, i.e., it is not affixed to the band 110. The left flap 114 is affixed to the band 110. It will be understood that the flaps 112, 114 can be the same and mirror images of each other on opposite sides of the garment. The flap 112 has a generally trapezoid shape with a bottom side 131 that is substantially parallel with the bottom side of the band 110. The vertical sides 132, 133 being essentially perpendicular to the bottom side 131. The top side 134 slopes downwardly to the front vertical side 133. In the free position, the flap 112 is only connected to the rear panel 108 at the rear side 132. The rear side 132 has a height that is equal to the height of the rear panel 108 whereat the flap 112 is connected to the rear panel. In another example, the flap 112 is connected to the seam whereat the front panel 108 and the rear panel 106 are connected. In another example, the rear side 133 has a height less than the height of the rear panel 106 at the location whereat the rear side 133 is connected. The rear side 133 will have a height greater than half the height of the rear panel 106, where connected.

A connector 137 releasably connects the flap 112 to the band 110. The connector can be a hook and loop connector. The hook part 135 is fixed to the inner side or surface 112A of the flap 112 adjacent the front side 132. The loop part 136 is fixed to the front face of the band 110. In an example, the hook part 135 and loop part 136 each have a height of about half inch. The hook part 135 has a length of about one and half inch. The loop part 136 can extend across the entire front length of the band 110. In another example, the loop part 136 extends about one-third the length of the band 110. In another example, a break in the loop part 136 is located at the midpoint of the band 110.

In use, the wearer grips the flap 112 and pulls the free front end side 133 to align the hook part 135 with the loop part 136. The wearer stretches the flap 112 to create a tension in the fabric of the flap and then fixes the hook and loop parts 135, 136 to connect the free end of the flap to the band 110. The shape of flap 112 distributes the tension from the front side end of the flap to the entire height of the rear panel while pulling the band 110 tighter about the torso of the wearer. Any excess material of at least one of the front panel 108, rear panel 106, and/or band 110 under the flap 112 can fold comfortably at the sides of the wearer. As a result, the circumferential size of the band 110 and the garment 200 as a whole can be adjusted to fit the wearer's torso and the comfort level of the wearer. The circumferential size and tension of the garment 200 are adjustable such that the garment can be individualized for any wearer.

The wearer can attach drainage fluid storage or holding assembly 250 to medical garment 200. The wearer connects drainage tube end 262 to inlet nozzle 256. Drainage tube end 264 can be connected to a shunt and implanted at the surgical site to be drained during surgery. Next, the wearer grasps container 252 and positions container 252 such that hook tab or member 271 abuts and contacts one or more of loop strips 210. The wearer presses on hook tab or member 271 to cause engagement of hooks on hook tab 271 with the loops of loop strip 210. Container 252 is now retained to mastectomy garment 200. The wearer can remove the plug 259 from outlet nozzle 258 and squeeze or compress flexible container 252 forcing air out from container 252 through outlet nozzle 258. Plug 259 is then replaced in outlet nozzle 258 creating a vacuum within container 252. Container 252 is formed so that it is biased to return to its normal non-compressed state. Compressing container 252 and then plugging outlet nozzle 258 with plug 259 creates a vacuum or suction within container 252. A continuous suction fluid communication path 214 is formed from container 252, inlet nozzle 256 and drainage tube 260 to the surgical site. Suction fluid communication path 214 allows for the vacuum within container 252 to continuously draw surgical drainage fluid from the surgical site through drainage tube 260, nozzle 258 and into container 252 where it is held or stored.

Figure 14:
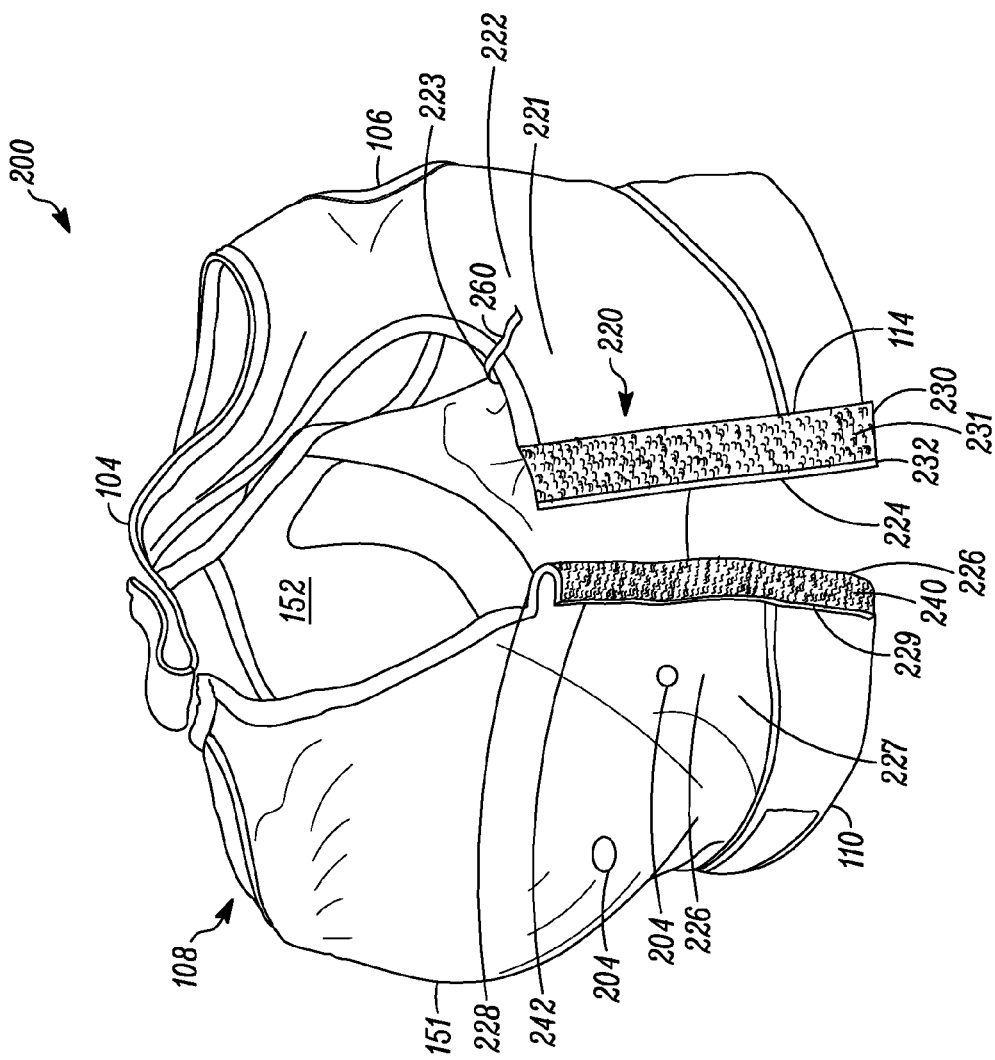
FIG. 14 is a side view of the medical garment in accordance with an example embodiment.

FIG. 14 shows a side view of the medical garment 200 without the flap 114 that connects the front of the band 110 and illustrating closure 220. In FIG. 14, closure 220 is shown in the open position. When closure 220 is opened, the front panel 108 and the rear panel 106 on the side of the wearer can move apart from each other creating opening 226. This will ease the ability to take off and put on the post-medical procedure, e.g., mastectomy, garment 200. In the illustrated example, closure 220 is a hook and loop fastener. Back panel 106 further includes a left side portion 221 with an outer surface 222, inner surface 223 and an end 224. Front panel 108 further includes a left side portion 226 with an outer surface 227, inner surface 228 and an end 229. Closure 220 has a wing 230 that is attached to back panel 106. Wing 230 extends from left side portion 221 at seam 144 to end 224. Loop part 231 can be attached to wing 230 on outer surface 222. In an embodiment, wing 230 and loop part 231 can be about one inch wide and extend along the length of end 224. In an example, the loop part 231 has a circumferential dimension, when worn, of greater than 1 inch and in some examples at least 2 inches. A narrow border 232 without loops is located along wing 230 between end 224 and loop part 231. Closure 220 has a hook part 240 that attached to front panel 108. Hook part 240 is fixed to the inner side or surface 228 along end 229. In an embodiment, hook part 240 can be about one inch wide and extend along the length of end 229. The hook part 240 can have the same dimensions as the loop part 231. A narrow border 242 without hooks is located along the length of end 224 between end 224 and hook part 240. In an example, the closure 220 is only on one side of mastectomy garment 200. In another example, a closure 220 can be located on each side of mastectomy garment 200.

In use, the wearer places a right arm through the opening under strap 102 and wraps front panel 108 and back panel 106 around their torso. The wearer grasps wing 230 and left side portion 226 and pulls on both to align the loop part 231 with the hook part 240. The wearer stretches front and back panels 106 and 108, respectively to create a tension in the fabric of the then fixes the hook and loop parts 240 and 231 to connect the front panel 108 to the back panel 109. The loop part 240 extends far enough so that loop part 240 fully engages the hook part 231. The shape of wing 230 distributes the tension from the front panel 108 to the entire height of the rear panel 106 while pulling the front panel 106 tighter about the torso of the wearer. As a result, the circumferential size of the mastectomy garment 200 as a whole can be adjusted to fit the wearer's torso and the comfort level of the wearer. The circumferential size and tension of the garment 200 are adjustable such that the garment can be individualized for any wearer. Closure 220 allows a wearer with limited mobility to take mastectomy garment 200 on and off with less effort.

The front panel 108 includes a fabric cover 151 that extends the entire size of the front panel. Fabric cover 151 is at least one layer of a stretchable, vertically and horizontally, fabric that can provide tension and compression to the front of the wearer. The stretchable fabric can be a knit material that can include LYCRA™, spandex, or other synthetic stretchable polymer. In an example, the resilient stretchable material is up to 10% of the content of the fabric. Other wicking material can be used in the fabric cover, e.g., COOLMAX™. Cover 151 extends the entire extent of the front panel and it connects to the rear panel 106. Cup assembly 152 is positioned beneath the cover 151 and is partially visible in FIG. 14. The cup assembly 152 is not visible in FIGS. 13A and 13B as the cover 151 completely covers the cup assembly 152 but the cup assembly 152 is form holding (e.g., semi-rigid). Hence, the cup assembly 152 gives a shape to the front panel 108 which would not exist due to the fabric cover alone. The cup assembly 152 defines two distinct cups 153, 154 (see, FIG. 15 for a better view of the cups) for receiving the breasts of a wearer. The cup assembly 152 can support and secure the breasts in place, particularly when the wearer as a larger cup size. The two individual cups 153, 154 can individually encapsulate the wearer's breasts.

Figure 15:
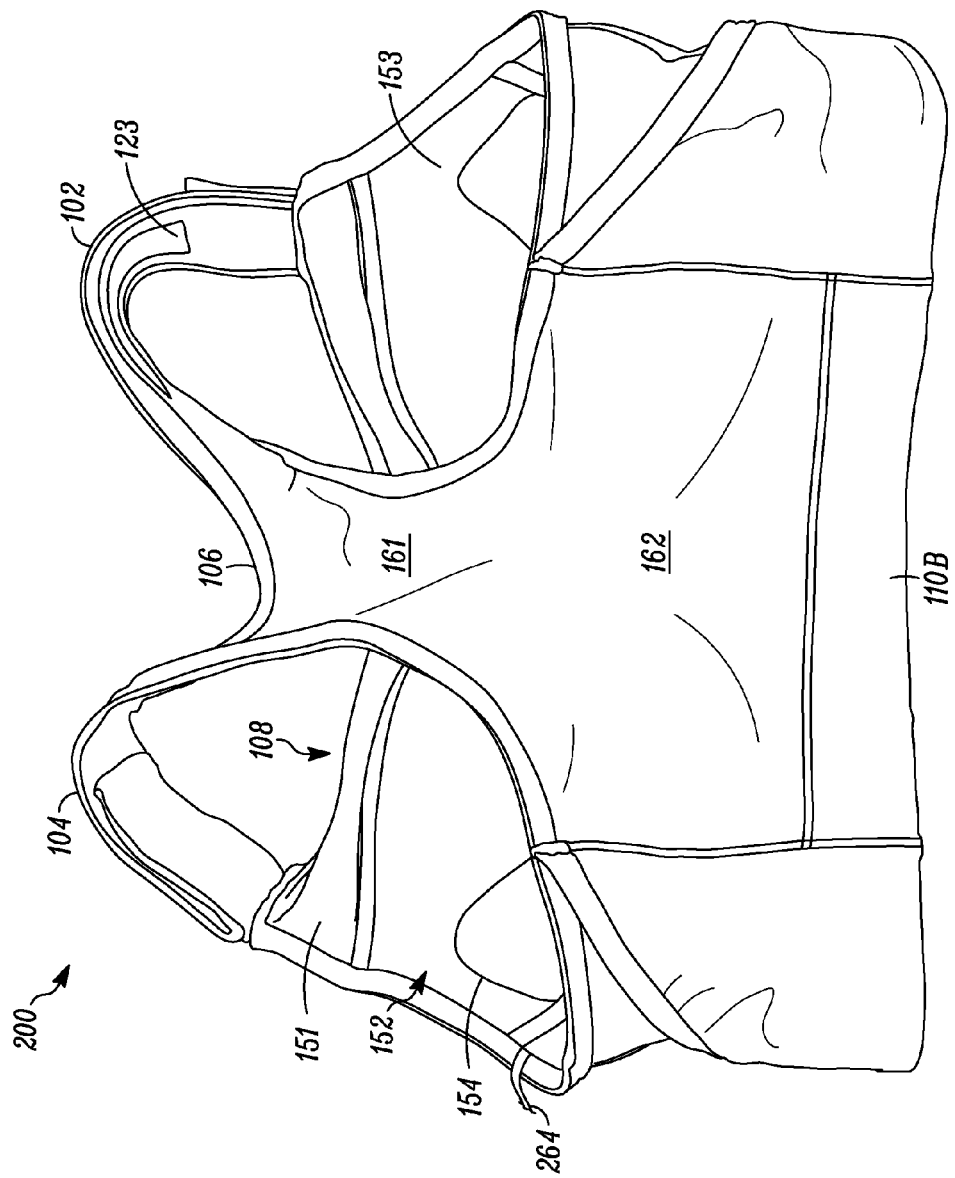
FIG. 15 is a rear view of the medical garment in accordance with an example embodiment.

FIG. 15 shows a rear view of the medical garment 200 including the rear band portion 110B, which can have a stronger elastic strength than the remainder of the band. The rear panel 106 includes a narrow upper portion 161 that can seamlessly transition into the straps 104, 106. Upper portion 161 is sized such that it essentially lays between the scapulae of the wearer and not interfere or chaff the user. The rear panel 106 includes a lower portion 162, which can be an integral fabric with the upper portion 161. The lower portion 162 has a height that extends from essentially beneath the wearer's scapulae and to essentially beneath the circumferential line beneath the wearer's breasts. Accordingly, the shape of the upper portion 161, the lower portion 162, straps 102, 104, and the top part of the front panel 108 to not interfere with freedom of movement of the arms and shoulders of the wearer.

Figure 16:
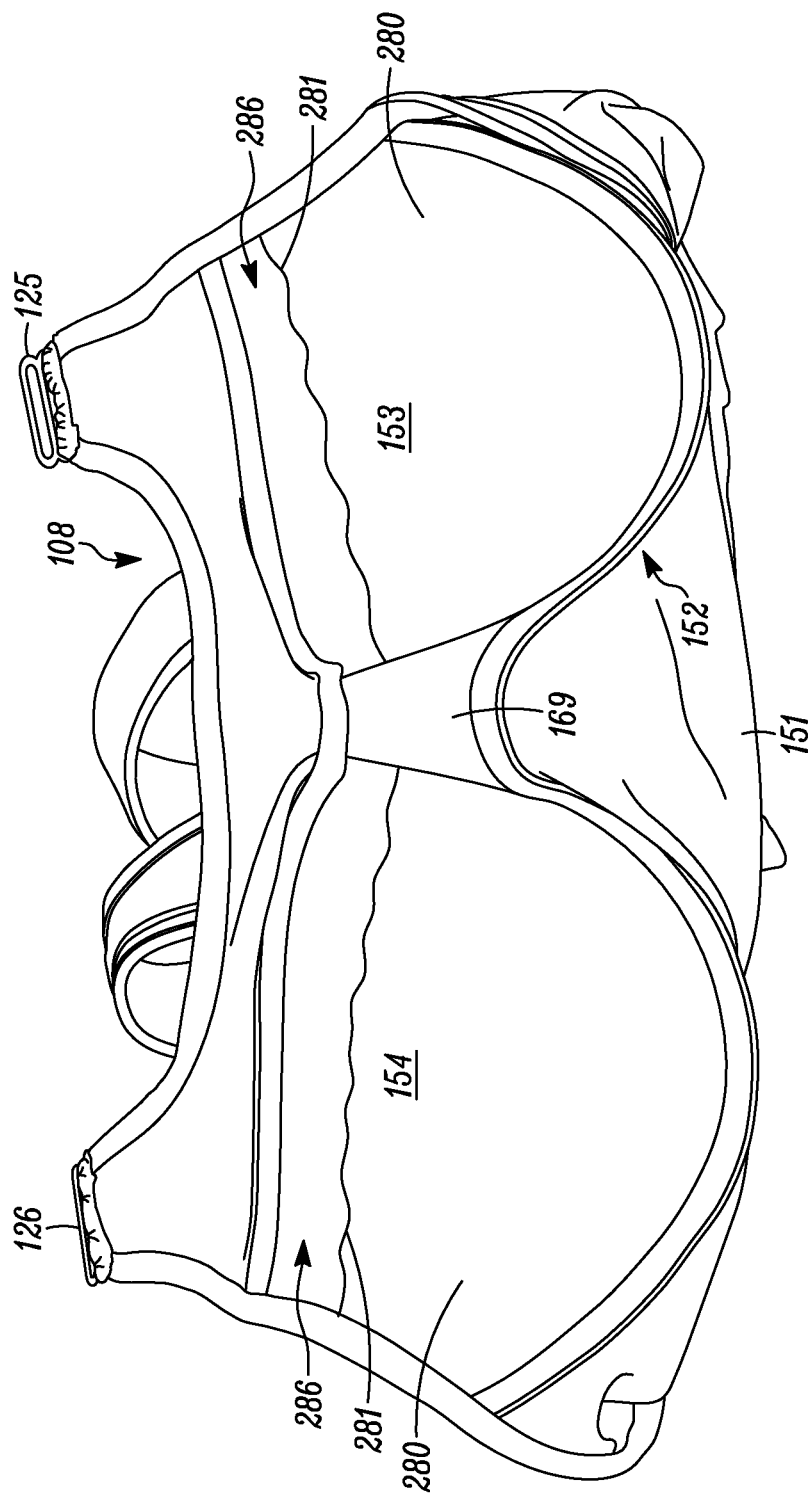
FIG. 16 is an interior view of the front of the medical garment in accordance with an example embodiment.

FIG. 16 shows a rear view of the front panel 108 including the cover 151 and the cup assembly 152, i.e., the rear panel is removed to more clearly show the cup assembly 152. The right and left cups 153 and 154 can be sized to fit a woman's breast size and individually encapsulate a wearer's breast. Thus, the inventor's of the present invention have found that a cup, e.g., A, B, C, D, DD, etc. that matches a wearer's breast size with a compressive cover, i.e., 151, provides a more comfortable fit and secures the breasts. The cup assembly 152 includes a bridge 169 is positioned between the cups 153, 154. The bridge 169 has the less height as compared to the remainder of the cup assembly. The bridge is essentially flat and narrower at the top than at the bottom. The bridge 169 is a semi-rigid fabric, in an example. The bridge 169 acts to hold the cups 153, 154 laterally in place. The bridge 169 is rigid to such an extent that it does not allow the cups 153, 154 to move laterally relative to each other, yet allows the cups to move forward and rearward. As a result, the cups 153,154 individually encapsulate the wearer's breasts prior to compression by the outer fabric cover 151 with the bridge 169 holding the two cups 153, 154 in place relative to each other.

Figure 17:
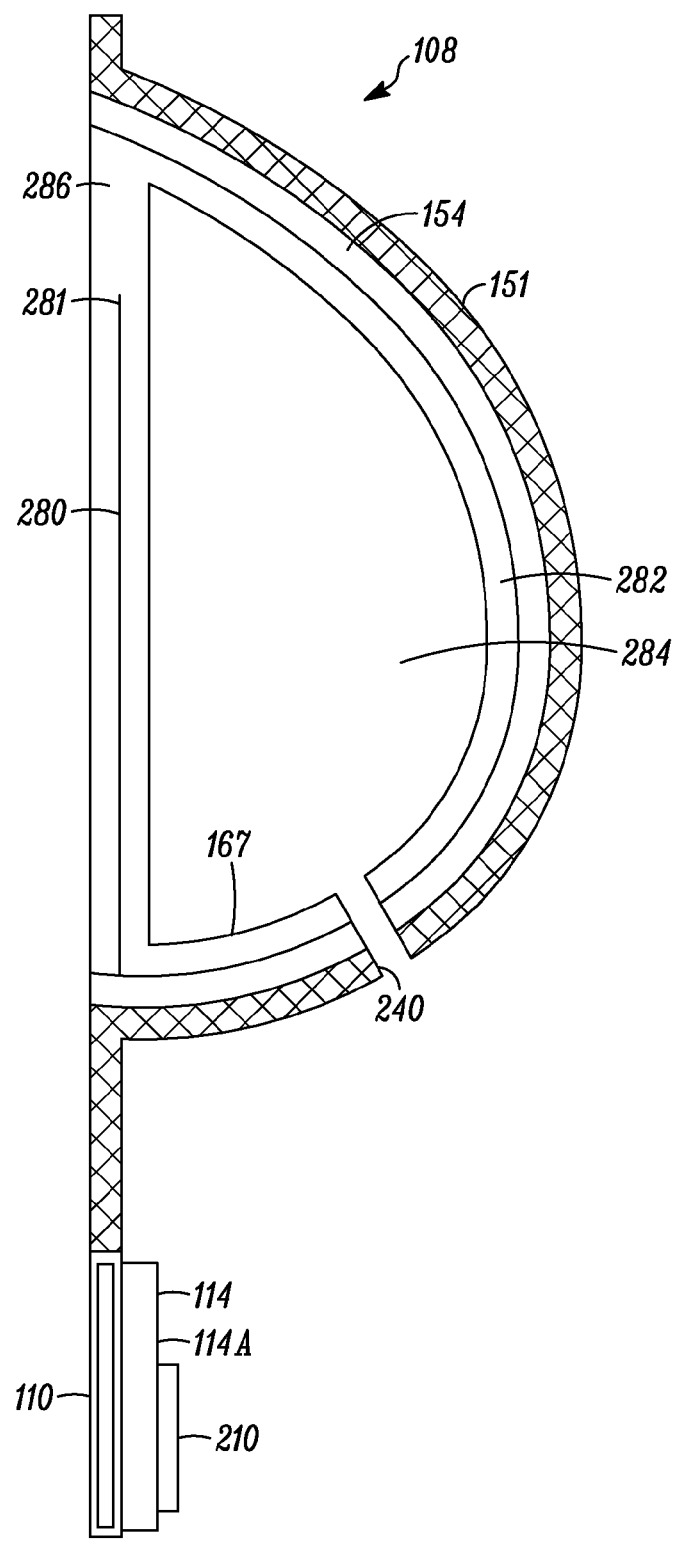
FIG. 17 is a cross-sectional view of the medical garment in accordance with an example embodiment.

With additional reference to FIG. 17, a cross-sectional view of cup 154 is shown. The front panel 108 includes the front cover 151 overlying the entire cup 154. The flap 114 is affixed to the band 110 beneath the cup 154. Loop part 210 is affixed to flap outer side or surface 114A. Aperture 204 is shown extending through front cover 151 and cup 154. Cup assembly 152 can further include a lining or wall 280 of fabric that is sewn into each of cups 153 and 154. In an example, the lining can be a cotton material, e.g., a cotton mesh. Lining or wall 280 has an upper edge 281. Lining or wall 280 and cups 153, 154 define a prosthetic pocket 282 within each of cups 153 and 154. Lining or wall 280 is attached to the outer periphery of cups 153 and 154 such that the center of lining or wall 280 is seamless to prevent irritation of the wearer. An opening 286 is located at upper edge 281 between lining or wall 280 and cups 153, 154. In an example, the opening is at an outer part of the top edge. The opening may not extend the entire width of the cup. The opening may only extend half or less than the top dimension of the cup. The opening may only extend a third of less of the top dimension of the cup. In an example, the opening extends downwardly from one corner of the top dimension to provide an adequate opening to insert the prosthetic. The opening can include a fastener to close the opening and secure the prosthetic therein. In an example, the fastener is an adhesive. In an example, the fastener is a hook and loop fastener. In an example, the fastener is a button. A prosthetic breast insert 284 can be placed into prosthetic pocket 282 through opening 286. Prosthetic breast insert 284 is used to simulate a real breast and provide a more natural look for the wearer. A variety of materials can be used for prosthetic breast insert 284. In one example, prosthetic breast insert 284 can be constructed with silicone gel covered by a plastic skin. Prosthetic breast insert 284 can be formed in a range of shapes and sizes in order to closely simulate the shape of the wearer. Medical garment 200 can be worn with or without prosthetic breast insert 284.

It will be within the scope of the present disclosure to provide a prosthetic that is fixed in the cup without an opening.

Figure 18:
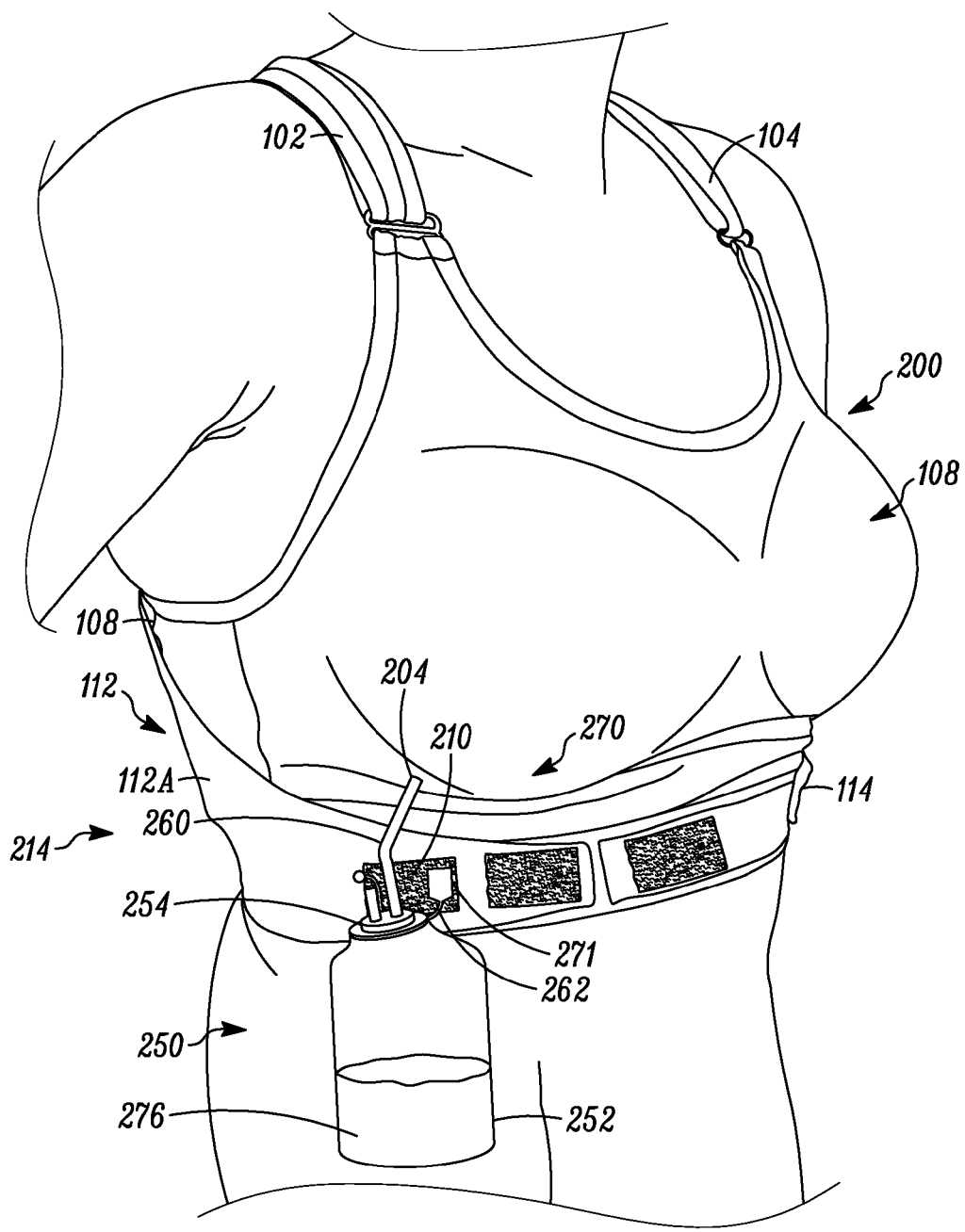
FIG. 18 is a view of the medical garment being worn during use in accordance with an example embodiment.

FIG. 18 shows the medical garment 200 being worn during use with the shoulder straps 102, 104 over the shoulders of the wearer and closure 220 retaining front panel 108 and back panel 106 with the wearer's breasts being held (lifted, encapsulated and then compressed) in the front panel 108. The side flaps 112, 114 assist in tightening the garment around the wearer's torso. The wearer can attach drainage fluid storage or holding assembly 250 to medical (e.g., mastectomy) garment 200. The wearer connects drainage tube end 262 to inlet nozzle 256. Drainage tube end 264 can be connected to a shunt and implanted at the surgical site to be drained during surgery. Next, the wearer grasps container 252 and positions container 252 such that hook tab or member 271 abuts and contacts one or more of loop strips 210. The wearer presses on hook tab or member 271 to cause engagement of hooks on hook tab 271 with the loops of loop strip 210. Container 252 is now retained to medical garment 200. The wearer can remove the plug 259 from outlet nozzle 258 and squeeze or compress flexible container 252 forcing air out from container 252 through outlet nozzle 258. Plug 259 is then replaced in outlet nozzle 258 creating a vacuum within container 252. Container 252 is formed so that it is biased to return to its normal non-compressed state. Compressing container 252 and then plugging outlet nozzle 258 with plug 259 creates a vacuum or suction within container 252. A continuous suction fluid communication path 214 is formed from container 252, inlet nozzle 256 and drainage tube 260 to the surgical site. Suction fluid communication path 214 allows for the vacuum within container 252 to continuously draw surgical drainage fluid 276 from the surgical site through drainage tube 260, nozzle 258 and into container 252 where it is held or stored.

The wearer can remove and empty drainage fluid storage or holding assembly 250. The wearer disconnects drainage tube end 262 from inlet nozzle 256. The wearer grasps hook tab or member 271 and pulls on hook tab or member 271 to cause disengagement of hooks on hook tab 271 with the loops of loop strip 210. Container 252 is now free from mastectomy garment 200. The wearer can position flexible container 252 such that cap 254 and inlet nozzle 256 are pointing downward over a fluid disposal location such as a sink. The wearer squeezes or compress flexible container 252 forcing drainage fluid 276 out from container 252 through inlet nozzle 256. The wearer continues to squeeze container 252 until container 252 is emptied of drainage fluid 276. Drainage fluid storage or holding assembly 250 can then be reattached to mastectomy garment 200 in the same manner as previously described.

Figure 19:
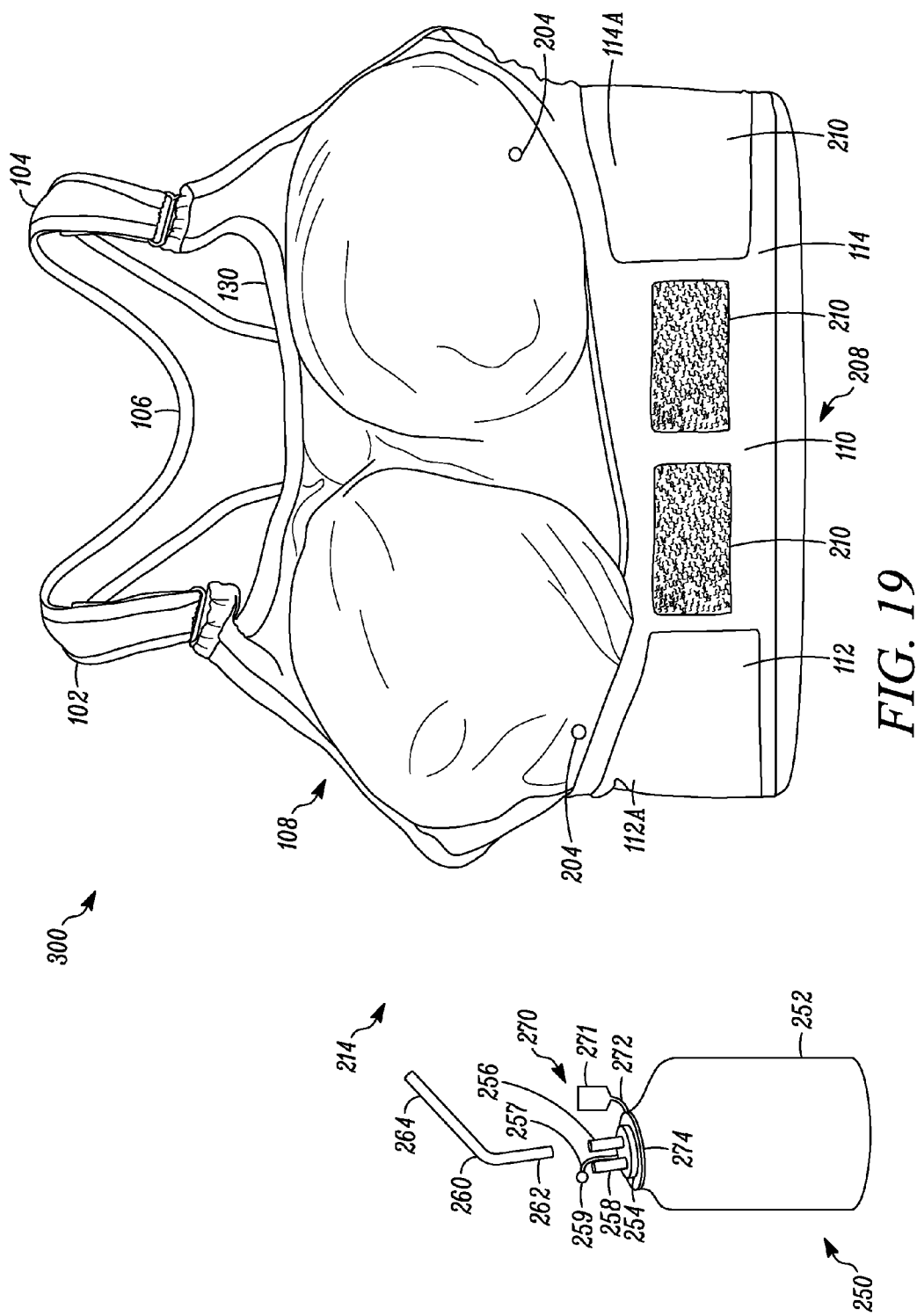
FIG. 19 is a front view of another embodiment of a medical garment in accordance with an example embodiment.

FIG. 19 shows a front view of another embodiment of a medical garment 300. Medical garment 300 is similar to medical garment 200 except that hook strips 210 have been removed from flaps 112 and 114 and affixed to band 110. Flaps 112 and 114 in FIG. 19 have been shortened in length such that a wider portion of band 110 is visible. The circumferential tensioning or tightening structure 208 of flaps 112, 114 and pull the rear and front panels 106, 108 together to reduce the circumferential size of the garment. Hook part 135 and loop part 136 hold flaps 112 and 114 in the same manner as previously described for mastectomy garment 200. The wearer can position drainage container assembly 250 such that hook tab or member 271 abuts and contacts one or more of loop strips 210 affixed to band 110. The wearer presses on hook tab or member 271 to cause engagement of hooks on hook tab 271 with the loops of loop strip 210. Container 252 is now retained to medical garment 300.

Figure 20:
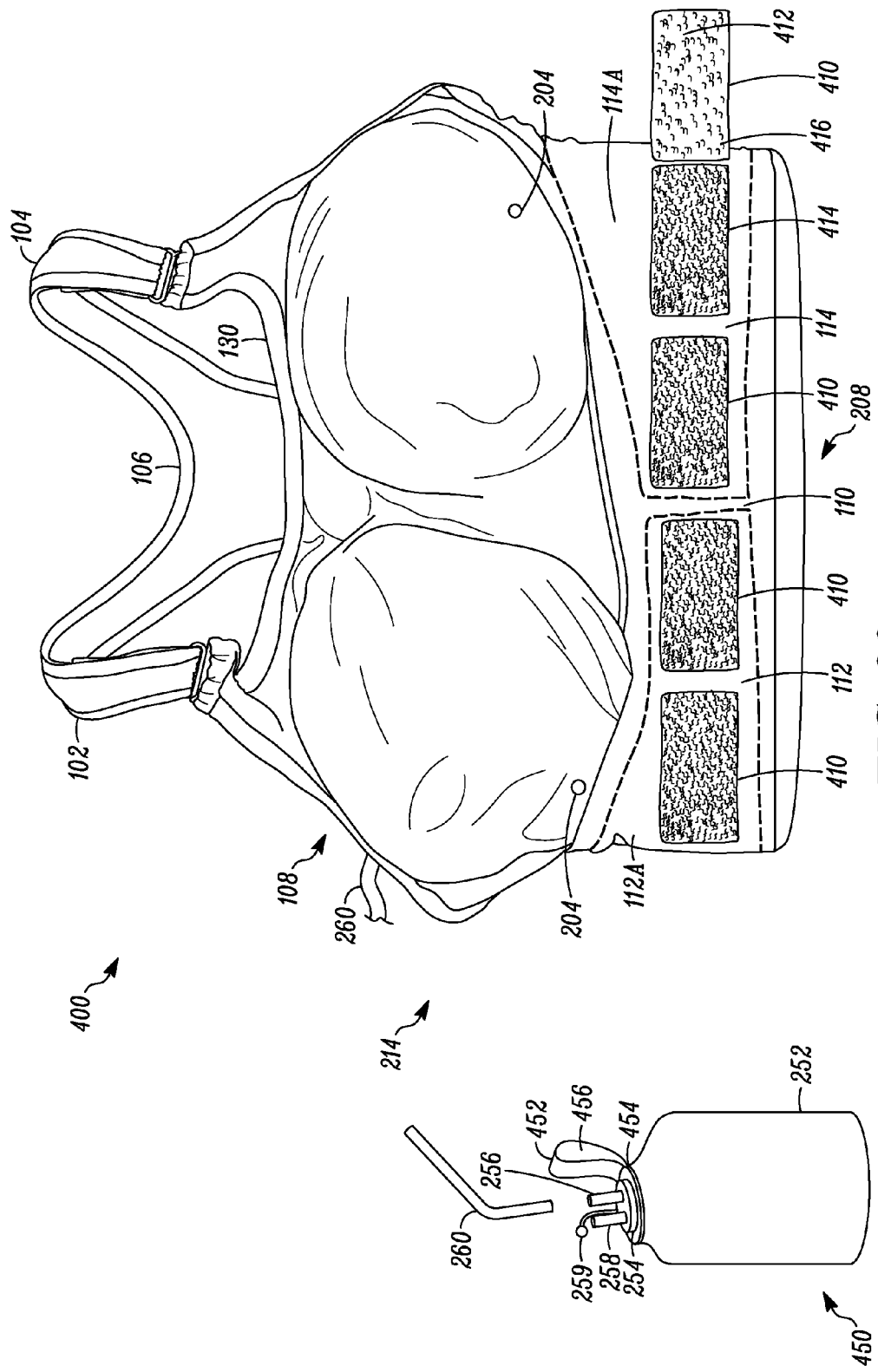
FIG. 20 is a front view of yet another embodiment of a medical garment in accordance with an example embodiment.

FIG. 20 shows a front view of an additional embodiment of a medical garment 400. Medical garment 400 is similar to medical garment 200 of FIG. 13A except that hook strips 210 have been replaced by hook and loop belts 410. In FIG. 20, four hook and loop belts 410 are shown. More or fewer hook and loop belts 410 can be used. Flaps 112, 114 are optional. Two of hook and loop fasteners or belts 410 are mounted to flap outer surface 112A and two of hook and loop belts 410 are mounted to flap outer surface 114A. Each hook and loop belt 410 includes a free hook part 412 and a fixed loop part 414. Loop part 414 is attached or fixed to band 110 by a suitable method such as sewing or by an adhesive. Loop part 414 contains a large number of loops. Hook part 412 is attached to band 110 along a seam 416. Hook part 412 can move about seam 146. Hook part 412 contains a large number of hooks. Hook part 412 can be attached and detached from loop part 414. The circumferential tightening structure 208 of flaps 112, 114 and pull the rear and front panels 106, 108 together to reduce the circumferential size of the garment. Hook part 135 and loop part 136 hold flaps 112 and 114 in the same manner as previously described for mastectomy garment 200. FIG. 20 can be modified to not have the flaps and include at least one side closure. The fasteners for the fluid collection system can be on the band beneath the cop assembly.

Drainage container assembly 450 includes a container 252 and a cap 254. A retaining band 452 has a retaining ring 454 that can be affixed between cap 254 and container 252. In an example, retaining ring 454 encircles the neck or opening of container 252. Cap 254 can be attached to container 252 via threads such that cap 254 is screwed onto container 252 thereby holding retaining ring 454 to container 252. Band 452 defines and encircles a slot 456. Drainage container assembly 450 can be attached to medical garment 400 by the wearer positioning drainage container assembly 450 such that band 452 is adjacent hook part 412. The wearer inserts hook part 412 through slot 456 and presses hook part 412 into contact with loop part 414 causing the engagement of the hooks on hook part 412 with the loops of loop part 414. Retaining band 452 is now firmly held by belt 410 causing drainage container assembly 450 to be retained to medical garment 400. The wearer may then connect drainage tube 260 to inlet nozzle 256. Drainage container assembly 450 can be removed from medical garment 400 by the wearer lifting hook part 412 away from loop part 414 and sliding hook part 412 out of engagement with retaining bad 452 and disconnecting drainage tube 260 from inlet nozzle 256.

Figure 21:
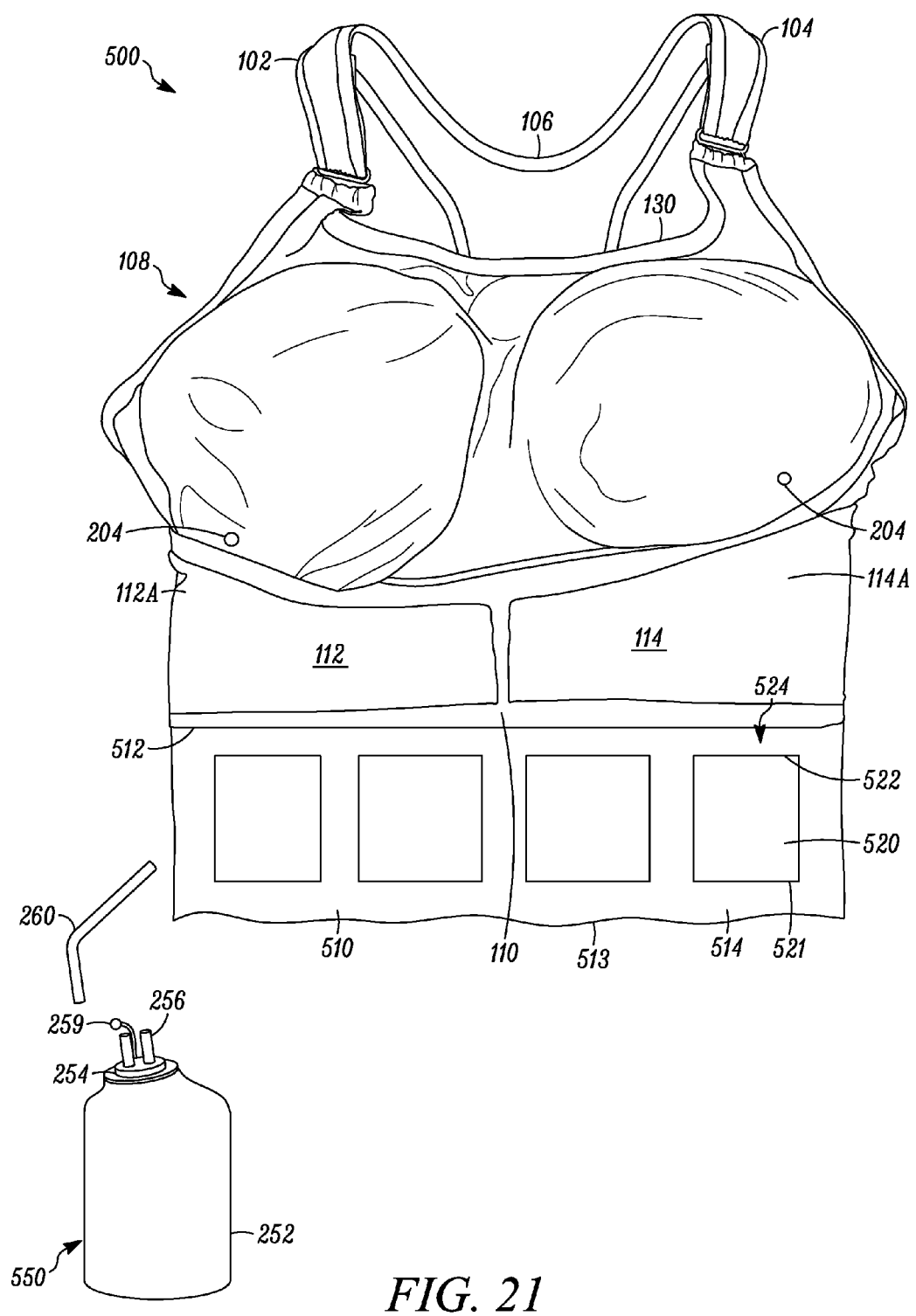
FIG. 21 is a front view of an additional embodiment of a medical garment in accordance with an example embodiment.

FIG. 21 shows a front view of one more embodiment of a medical garment 500. Medical garment 500 is similar to medical garment 200 of FIG. 13A except that hook strips 210 have been eliminated and a skirt 510 has been added. Skirt 510 is formed from a fabric material. Skirt 510 extends below and is attached to band 110. Skirt 510 is attached to band 110 by sewing. Skirt 510 has an upper edge 512 where it is attached to band 110, a bottom edge 513 and an outer surface 514. Several pockets 520 are attached to outer surface 514. Pocket 520 is defined by an apron 521 of fabric or material that is sewn to skirt 510 along three edges. One edge 522 is not sewn and defines an opening 524 between skirt 510 and edge 522. In FIG. 21, four pockets 520 are shown. More or fewer pockets 520 can be used.

Drainage container assembly 550 includes a container 252 and a cap 254. Drainage container assembly 550 can be attached to medical garment 500 by the wearer positioning drainage container assembly 550 into one of pockets 520. The wearer places container 252 through opening 524 into pocket 520. The wearer may then connect drainage tube 260 to inlet nozzle 256. Drainage container assembly 550 can be removed from mastectomy garment 500 by the wearer removing container 252 from pocket 520 and disconnecting drainage tube 260 from inlet nozzle 256.

While many of the above examples describe hook and loop connectors in certain configurations where the hook part and the loop part are on the certain structures. It will be understood that the hook and loop parts could be reversed and positioned in the other structure. The hook and loop connector can be VELCRO™. It is further understood that a plurality of hook and loop fasteners can be provided to support a plurality of fluid containers or fluid bulbs.

The present inventor has recognized the need to improve women's post medical procedure (e.g., mastectomy, lumpectomy, lymphadenectomy, cardiac surgery, lung surgery, back surgery, or other upper torso medical procedures) apparel by providing a garment that individually lifts a woman's breasts, individually encapsulates each breast in an individual cup, compresses the breasts to hold then in place, and includes an easily removable fluid storage device to hold surgical drainage fluid in the days after the medical procedure, e.g., mastectomy surgery. The present garment reduces the level of discomfort experienced after medical procedures surgery and may assist in improving patient outcomes. It is also believed that wearing a properly fitting and supporting post-procedure garment may reduce the risk or amount of post-procedure scarring. The presently described garment holding a patient's upper torso in position, e.g., breast tissue, with a relatively constant compression may also assist in improving patient outcomes. Patient outcomes can be measured in patient compliance with wearing the garment, possible reduction in the increase in scarring, and/or reduced swelling or liquid retention.

It will further be recognized that the apertures 190A-190F described above with regard to FIGS. 1-6 can also be incorporated into the examples shown and described with respect to FIGS. 13-21. It will also be recognized that various garments described herein may also be made without apertures 190A-190F. If a garment includes an aperture, then the aperture may be provided in the softer fabric areas only and not in the molded cup portions of the garment.

It will also be recognized that any embodiment described herein includes a side flap, e.g., the embodiments of FIGS. 1A, 1B, 6, 11, 12, 13A, 13B, and 18, can be changed to include the side closure structure of FIG. 14 instead of a side flap type closure. It will also be recognized that a side closure need only be positioned on one side of the garment.

The presently described garments may provide circumferential compression that may be benefit to an exercise wearer or a post-medical procedure wearer. The materials of the garment can be selected and sized to an individual to provide compression circumferentially around the wearer's torso. In the case of a post-surgical garment, such compression may reduce the risk of swelling and/or reduce the risk of lymphedema. In the case of medical procedures where it is desired to reduce movement or variable pressure on the chest of the wearer (e.g., a patient), the side closure examples described herein may be a benefit to the wearer. In some cardiac procedures, the sternum must be broken. Movement or variable pressure may be painful to the patient. The side closure example may reduce the discomfort to the patient.

The presently described garments may also be of benefit to women who have reconstructive surgery or breast augmentation. The present garment may stabilize tissue and or implants and may reduce complications. The present garments can be adjusted to specifically fit a patient. In an example, the garment for a patient may be adjusted prior to the surgical procedure, then placed on the patient more easily than traditional brassieres, e.g., using the releasable straps and/or side openings. Moreover, some traditional brassieres that may be used in post-medical situations have a center closure, i.e., between the cups. A potential drawback to these brassieres is they pull the breast tissue to the center or midline of a patient for closure and, perhaps, after the brassiere is closed and worn by the patient. Examples of the present invention described herein may have a side opening that allows ease of adornment while providing desired security, compression and support of breast tissue.

In an example, a post-medical garment can comprise: a rear panel; a front panel connected to the rear panel, the front panel including an elastic, outer cover fabric and a cup assembly to receive the breasts of the wearer; an elastic band beneath the cup assembly; a first strap extending upwardly from the rear panel to the front panel; a second strap extending upwardly from the rear panel to the front panel; a circumferential tightening structure to tighten the circumference of the garment around the torso of the user; a skirt extending below the circumferential tightening structure fluid; and the skirt having at least one pocket. The circumferential tightening structure can support drainage bulbs or a fluid collection system. In an example, the fluid storage device can be inserted and removed from the pocket.

In an example, a post-medical procedure surgical garment can comprise a rear panel; a front panel connected to the rear panel, the front panel including an elastic, outer cover fabric and a cup assembly to receive the breasts of the wearer; at least one aperture extending through the front panel; an elastic band beneath the cup assembly; a first strap extending upwardly from the rear panel to the front panel; a second strap extending upwardly from the rear panel to the front panel; a circumferential tightening structure to tighten the circumference of the garment around the torso of the user; the circumferential tightening structure including at least one side flap that in a first, free position is connected to only one of the front panel and the rear panel and in a second, tensioning position has another end that connects to the other of the front panel and rear panel; the side flap having an inner surface and an outer surface, a hook part of a first connector attached to the inner surface and a hook and loop belt attached to the outer surface. A drainage bulb can be supported by the belt. In an example, a loop part of the first connector is attached to the elastic band. In an example, a fluid storage device is removably attached to the hook and loop belt. The fluid storage device has a retaining band that is received by the hook and loop belt.

It will be understood that in various embodiments, the garment does not require the side flaps but has a side closure system (e.g., FIG. 14). Fasteners for a fluid collection system can be provided on the band beneath the cups. For example, the side flaps 112 and 114 of FIGS. 13A and 13B can be removed and a fastener system for securing the collection devices to the band of the garment. FIG. 20 shows an embodiment where the side flaps are shown as optional.

Thus, post-medical procedure garments, such as bras, support shirts, and tankinis, and methods of their use have been described. Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

What is claimed is:
1. A post-medical procedure garment, comprising:
a rear panel;
a front panel connected to the rear panel, wherein the front panel includes a cup assembly defining two distinct cups to receive the breasts of the wearer and an elastic, outer cover fabric extending across the cup assembly;
an elastic band attached to the rear panel and the front panel, wherein the elastic band is positioned beneath the cup assembly of the front panel;
a first strap extending upwardly from the rear panel to the front panel;

a second strap extending upwardly from the rear panel to the front panel;

a circumferential tightening structure adjustable over the elastic band to tighten a circumference of the garment around the torso of the user, wherein the circumferential tightening structure includes at least one side flap that is stretchable and extendable over less than half the width of the front panel; and a fluid storage device removably attached to the circumferential tightening structure.

2. The post-medical procedure garment of claim 1, wherein the fluid storage device has a container and a cap.

3. The post-medical procedure garment of claim 2, wherein the cap has an inlet nozzle.

4. The post-medical procedure garment of claim 3, wherein the inlet nozzle is connected to one end of a drainage tube.

5. The post-medical procedure garment of claim 1, wherein a hook and loop connector connects the fluid storage device to the circumferential tightening structure.

6. The post-medical procedure garment of claim 5, wherein the at least one side flap in a first, free position is connected to only one of the front panel and the rear panel and in a second, tensioning position has another end that connects to the other of the front panel and rear panel, a loop part of the connector attached to at least one flap and a hook part of the connector attached to the fluid storage device.

7. The post-medical procedure garment of claim 6, wherein the fluid storage device has an attached tab, the hook part of the connector attached to the tab.

8. The post-medical procedure garment of claim 1, wherein at least one aperture extends through the cup assembly.

9. The post-medical procedure garment of claim 8, wherein a drainage tube is positioned to extend through the aperture.

10. The post-medical procedure garment of claim 1, wherein a closure joins the front panel to the rear panel along a side of a torso of a wearer.

11. The post-medical procedure garment of claim 10, wherein the closure is a hook and loop connector.

12. A post-medical procedure garment, comprising:
a rear panel;
a front panel connected to the rear panel, the front panel including a cup assembly including two distinct cups to receive the breasts of the wearer and an elastic, outer cover fabric extending over the cup assembly;
an elastic band coupled to the rear panel and the front panel, wherein the elastic band extends beneath the cup assembly;
a first strap extending upwardly from the rear panel to the front panel;
a second strap extending upwardly from the rear panel to the front panel;
a circumferential tightening structure extendable over at least a portion of the elastic band to tighten a circumference of the garment around the torso of the user; and
a fluid storage device removably attached to the elastic band.

13. The post-medical procedure garment of claim 12, wherein the fluid storage device has a container and a cap.

14. The post-medical procedure garment of claim 13, wherein the cap has an inlet nozzle, wherein the inlet nozzle is connected to one end of a drainage tube, and wherein a hook and loop connector connects the fluid storage device to the elastic band.

15. The post-medical procedure garment of claim 14, wherein the fluid storage device has an attached tab, the hook part of the connector attached to the tab.

16. The post-medical procedure garment of claim 12, wherein at least one aperture extends through the cup assembly and wherein a drainage tube is positioned to extend through the aperture.

17. The post-medical procedure garment of claim 12, wherein a closure joins the front panel to the rear panel along a side of a torso of a wearer.

18. The post-medical procedure garment of claim 12, wherein the cup assembly contains a prosthetic pocket that is adapted to receive a prosthetic insert.

19. A post-medical procedure garment, comprising:
a rear panel;
a front panel connected to the rear panel, the front panel including a cup assembly defining two distinct cups to receive the breasts of the wearer and an elastic, outer cover fabric extending over the cup assembly;
at least one aperture extending through the cup assembly;
an elastic band beneath the cup assembly;
a first strap extending upwardly from the rear panel to the front panel;
a second strap extending upwardly from the rear panel to the front panel; and
a circumferential tightening structure to tighten a circumference of the garment around the torso of the user, wherein the circumferential tightening structure includes at least one side flap that in a first, free position is connected to only one of the front panel and the rear panel and in a second, tensioning position has another end that connects to the other of the front panel and rear panel, wherein the side flap includes an inner surface and an outer surface, and wherein the inner surface includes a first connector having a hook part and the outer surface includes a second connector having a loop part.

20. The post-medical procedure garment of claim 19, wherein a loop part of the first connector is attached to the elastic band.

21. The post-medical procedure garment of claim 19, wherein a fluid storage device is removably attached to the side flap.

22. The post-medical procedure garment of claim 21, wherein a hook part of the second connector is coupled to the fluid storage device.

23. The post-medical procedure garment of claim 19, wherein a drainage tube can be positioned to extend through the aperture.

24. The post-medical procedure garment of claim 19, wherein a closure joins the front panel to the rear panel along a side of a torso of a wearer.

\* \* \* \* \*